(12) United States Patent
Scholz et al.

(10) Patent No.: US 7,947,494 B2
(45) Date of Patent: May 24, 2011

(54) **FUSION PROTEIN COMPRISING AN *E. COLI* CHAPERONE PROTEIN AND A HUMAN CHAPERONE PROTEIN**

(75) Inventors: Christian Scholz, Penzberg (DE); Elke Faatz, Huglfing (DE); Peter Schaarschmidt, Uffing (DE); Urban Schmitt, Oberhausen (DE)

(73) Assignee: Roche Diagnostics Operations, Inc., Idianapolis, IN (US)

( * ) Notice: Subject to any disclaimer, the term of this patent is extended or adjusted under 35 U.S.C. 154(b) by 0 days.

(21) Appl. No.: 12/166,574

(22) Filed: Jul. 2, 2008

(65) Prior Publication Data

US 2009/0042251 A1     Feb. 12, 2009

Related U.S. Application Data

(63) Continuation of application No. PCT/EP2006/012599, filed on Dec. 29, 2006.

(30) Foreign Application Priority Data

Jan. 3, 2006   (EP) .................................. 06000056
May 3, 2006   (EP) .................................. 06009106

(51) Int. Cl.
   *C12N 15/00*   (2006.01)
   *C07H 21/04*   (2006.01)
(52) U.S. Cl. ................................. 435/320.1; 536/23.4
(58) Field of Classification Search .................. None
   See application file for complete search history.

(56) References Cited

U.S. PATENT DOCUMENTS 6,207,420 B1   3/2001   Harrison et al.

FOREIGN PATENT DOCUMENTS

| CA | 2522221 A1 | 10/2004 |
|---|---|---|
| EP | 1516928 A1 * | 3/2005 |
| WO | 97/10253 A1 | 3/1997 |
| WO | 03/000877 A2 * | 1/2003 |
| WO | 03/000878 A3 | 1/2003 |

OTHER PUBLICATIONS

Suzuki et al., J. Mol. Biol. 328:1149-1160, 2003.*
Scholz et al., "Functional Solubilization of Aggregation-prone HIV Envelope Proteins by Covalent Fusion with Chaperone Modules", J. Mol. Biol. 345:1229-1241, 2005.*
Roof et al., "slyD, a Host Gene Required for x174 Lysis, Is Related to the FK506-binding Protein Family of Peptidyl-prolyl cis- trans-Isomerases", J. Biol. Chem. 269:2902-2910, 1994.*
Standaert et al., "Molecular cloning and overexpression of the human FK506-binding protein FKBP", Nature 346:671-674, 1990.*
Knappe et al., "Insertion of a Chaperone Domain Converts FKBP12 into a Powerful Catalyst of Protein Folding", J. Mol. Biol. 368:1458-1468, 2007.*
International Search Report issued May 2, 2007 in PCT Application No. PCT/EP2006/012599.
International Preliminary Report on Patentability issued Jan. 21, 2008 in PCT Application No. PCT/EP2006/012599.
Hottenrott, Sandra et al., The *Escherichia coli* SlyD Is a Metal Ion-regulated Peptidyl-prolyl cis/trans-Isomorase, The Journal of Biological Chemistry, Jun. 20, 1997, pp. 15697-15701, vol. 272, No. 25.
Kay, John E., Structure-function relationships in the FK506-binding protein (FKBP) family of peptidylprolyl cis-trans isomerases, Biochemistry Journal, 1996, pp. 361-385, vol. 314.
Maruyama, Tadashi et al., Archaeal Peptidyl Prolyl Cis-Trans Isomerases (PPIases) Update 2004, Frontiers in Bioscience, May 1, 2004, pp. 1680-1700, vol. 9.
Mogk, Axel et al., Mechanisms of Protein Folding: Molecular Chaperones and Their Application in Biotechnology, ChemBioChem, 2002, pp. 807-814, vol. 3.
Saul, F. A. et al., Structural and Functional Studies of FkpA from *Escherichia coli*, a cis/trans Peptidyl-prolyl Isomerase with Chaperone Activity, Journal of Molecular Biology, 2004, pp. 595-608, vol. 335.
Scholz, Christian et al., Cooperation of enzymatic and chaperone functions of trigger factor in the catalysis of protein folding, The EMBO Journal, 1997, pp. 54-58, vol. 16, No. 1.
Scholz, Christian et al., SlyD Proteins from Different Species Exhibit High Prolyl Isomerase and Chaperone Activities, Biochemistry, 2006, pp. 20-33, vol. 45.
Zhang, Jie Wei et al., A Role for SlyD in the *Escherichia coli* Hydrogenase Biosynthetic Pathway, The Journal of Biological Chemistry, Feb. 11, 2005, pp. 4360-4366, vol. 280, No. 6.

* cited by examiner

*Primary Examiner* — David J Steadman

(57) ABSTRACT

The invention discloses the cloning, expression and uses of a chimeric fusion protein with superior chaperone and folding activities compared to the wild type chaperones. This invention relates to a chimeric fusion protein encoded by a recombinant DNA molecule comprising nucleotide sequences coding for a polypeptide binding segment of a non-human chaperone protein and nucleotide sequences coding for an FK506 binding protein (FKBP) or an FK506-binding-protein-like domain (FKBP-like domain). In particular, this invention relates to a chimeric fusion protein encoded by a recombinant DNA molecule comprising nucleotide sequences coding for a polypeptide binding segment of a non-human chaperone protein and nucleotide sequences coding for a human FKBP type peptidyl-prolyl-cis/trans isomerase (PPIase), methods of producing these chimeric fusion proteins and their uses as folding helpers in the production of other proteins and in the process of the production of vaccines or pharmaceuticals, and as folding helpers for performing immunoassays.

1 Claim, 11 Drawing Sheets

A

B

A

B

A

B

A

B

A

B

A

B

US 7,947,494 B2

SEQUENCE LISTING

<160> NUMBER OF SEQ ID NOS: 27

<210> SEQ ID NO 1
<211> LENGTH: 196
<212> TYPE: PRT
<213> ORGANISM: Escherichia coli

<400> SEQUENCE: 1

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
            115                 120                 125

Asn Leu Lys Phe Asn Val Glu Val Ala Ile Arg Glu Ala Thr Glu
            130                 135                 140

Glu Glu Leu Ala His Gly His Val His Gly Ala His Asp His His
145                 150                 155                 160

Asp His Asp His Asp Gly Cys Cys Gly His Gly His Asp His Gly
                165                 170                 175

His Glu His Gly Gly Glu Gly Cys Cys Gly Lys Gly Asn Gly Gly
            180                 185                 190

Cys Gly Cys His
            195

<210> SEQ ID NO 2
<211> LENGTH: 107
<212> TYPE: PRT
<213> ORGANISM: Homo sapiens

<400> SEQUENCE: 2

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 3
<211> LENGTH: 113
<212> TYPE: PRT
<213> ORGANISM: Homo sapiens

<400> SEQUENCE: 3

Gly Val Gln Val Glu Thr Ile Ser Pro Gly Asp Gly Arg Thr Phe Pro
1               5                   10                  15

Lys Arg Gly Gln Thr Ala Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu His His His His
            100                 105                 110

His

```
<210> SEQ ID NO 4
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Val Gln Val Glu Thr Ile Ser Pro Gly Asp Gly Arg Thr Phe Pro
 1               5                  10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
        50                  55                  60

Gln Met Ser Val Gly Gln Arg Ala Lys Leu Thr Ile Ser Pro Asp Tyr
 65                 70                  75                  80

Ala Tyr Gly Gln Tyr Asp Glu Asn Leu Val Gln Arg Val Pro Lys Asp
                85                  90                  95

Val Phe Met Gly Val Asp Glu Leu Gln Val Gly Met Arg Phe Leu Ala
               100                 105                 110

Glu Thr Asp Gln Gly Pro Val Pro Val Glu Ile Thr Ala Val Glu Asp
            115                 120                 125

Asp His Val Val Asp Gly Asn His Met Leu Ala Gly Gln Asn Leu
        130                 135                 140

Val Phe Asp Val Glu Leu Leu Lys Leu Glu
145                 150

<210> SEQ ID NO 5
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Val Gln Val Glu Thr Ile Ser Pro Gly Asp Gly Arg Thr Phe Pro
 1               5                  10                  15

Lys Arg Gly Gln Thr Ala Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
        50                  55                  60

Gln Met Ser Val Gly Gln Arg Ala Lys Leu Thr Ile Ser Pro Asp Tyr
 65                 70                  75                  80

Ala Tyr Gly Gln Tyr Asp Glu Asn Leu Val Gln Arg Val Pro Lys Asp
                85                  90                  95

Val Phe Met Gly Val Asp Glu Leu Gln Val Gly Met Arg Phe Leu Ala
               100                 105                 110

Glu Thr Asp Gln Gly Pro Val Pro Val Glu Ile Thr Ala Val Glu Asp
            115                 120                 125

Asp His Val Val Asp Gly Asn His Met Leu Ala Gly Gln Asn Leu
        130                 135                 140

Val Phe Asp Val Glu Leu Leu Lys Leu Glu
145                 150
```

<210> SEQ ID NO 6
<211> LENGTH: 535
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Met Lys Val Ala Lys Asp Leu Val Val Ser Leu Ala Tyr Gln Val Arg
 1               5                  10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp Asp His Val
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His Asp His Asp His Asp
            340                 345                 350

Gly Gly Gly Ser Gly Gly Gly Ser Gly Gly Gly Ser Gly Gly Gly Ser
        355                 360                 365

-continued

```
Gly Gly Gly Ser Gly Gly Gly Thr Leu Thr Val Gln Ala Arg Gln Leu
            370             375                 380

Leu Ser Gly Ile Val Gln Gln Asn Asn Glu Leu Arg Ala Ile Glu
385             390                 395                 400

Ala Gln Gln His Leu Glu Gln Leu Thr Val Trp Gly Thr Lys Gln Leu
                405                 410                 415

Gln Ala Arg Glu Leu Ala Val Glu Arg Tyr Leu Lys Asp Gln Gln Leu
            420                 425                 430

Leu Gly Ile Trp Gly Cys Ser Gly Lys Leu Ile Cys Thr Thr Ala Val
            435                 440                 445

Pro Trp Asn Ala Ser Trp Ser Asn Lys Ser Leu Glu Gln Ile Trp Asn
            450                 455                 460

Asn Met Thr Trp Met Glu Trp Asp Arg Glu Ile Asn Asn Tyr Thr Ser
465                 470                 475                 480

Leu Ile His Ser Leu Ile Glu Glu Ser Gln Asn Gln Gln Glu Lys Asn
                485                 490                 495

Glu Gln Glu Leu Leu Glu Leu Asp Lys Trp Ala Ser Leu Trp Asn Trp
            500                 505                 510

Phe Asn Ile Thr Asn Trp Leu Trp Tyr His Gly His Asp His Asp His
            515                 520                 525

Asp His His His His His His
            530                 535
```

<210> SEQ ID NO 7
<211> LENGTH: 509
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 7

```
Met Gly Val Gln Val Glu Thr Ile Ser Pro Gly Asp Gly Arg Thr Phe
  1               5                  10                  15

Pro Lys Arg Gly Gln Thr Ala Val Val His Tyr Thr Gly Met Leu Glu
                20                  25                  30

Asp Gly Lys Lys Phe Asp Ser Ser Arg Asp Arg Asn Lys Pro Phe Lys
            35                  40                  45

Phe Met Leu Gly Lys Gln Glu Val Ile Arg Gly Trp Glu Glu Gly Val
        50                  55                  60

Ala Gln Met Ser Val Gly Gln Arg Ala Lys Leu Thr Ile Ser Pro Asp
65                  70                  75                  80

Tyr Ala Tyr Gly Gln Tyr Asp Glu Asn Leu Val Gln Arg Val Pro Lys
                85                  90                  95

Asp Val Phe Met Gly Val Asp Glu Leu Gln Val Gly Met Arg Phe Leu
            100                 105                 110

Ala Glu Thr Asp Gln Gly Pro Val Pro Val Glu Ile Thr Ala Val Glu
        115                 120                 125

Asp Asp His Val Val Asp Gly Asn His Met Leu Ala Gly Gln Asn
            130                 135                 140

Leu Val Phe Asp Val Glu Leu Leu Lys Leu Glu Gly Gly Ser Gly
145                 150                 155                 160

Gly Gly Ser Gly Gly Gly Ser Gly Gly Gly Ser Gly Gly Gly Ser Gly
                165                 170                 175

Gly Gly Gly Val Gln Val Glu Thr Ile Ser Pro Gly Asp Gly Arg Thr
            180                 185                 190
```

Phe Pro Lys Arg Gly Gln Thr Ala Val Val His Tyr Thr Gly Met Leu
            195                 200                 205

Glu Asp Gly Lys Lys Phe Asp Ser Ser Arg Asp Arg Asn Lys Pro Phe
        210                 215                 220

Lys Phe Met Leu Gly Lys Gln Glu Val Ile Arg Gly Trp Glu Glu Gly
225                 230                 235                 240

Val Ala Gln Met Ser Val Gly Gln Arg Ala Lys Leu Thr Ile Ser Pro
                245                 250                 255

Asp Tyr Ala Tyr Gly Gln Tyr Asp Glu Asn Leu Val Gln Arg Val Pro
                260                 265                 270

Lys Asp Val Phe Met Gly Val Asp Glu Leu Gln Val Gly Met Arg Phe
            275                 280                 285

Leu Ala Glu Thr Asp Gln Gly Pro Val Pro Val Glu Ile Thr Ala Val
        290                 295                 300

Glu Asp Asp His Val Val Asp Gly Asn His Met Leu Ala Gly Gln
305                 310                 315                 320

Asn Leu Val Phe Asp Val Glu Leu Leu Lys Leu Glu Gly Gly Gly Ser
                325                 330                 335

Gly Gly Gly Ser Gly Gly Gly Ser Gly Gly Ser Gly Gly Gly Ser
            340                 345                 350

Gly Gly Gly Thr Leu Thr Val Gln Ala Arg Gln Leu Leu Ser Gly Ile
            355                 360                 365

Val Gln Gln Gln Asn Asn Glu Leu Arg Ala Ile Glu Ala Gln Gln His
370                 375                 380

Leu Glu Gln Leu Thr Val Trp Gly Thr Lys Gln Leu Gln Ala Arg Glu
385                 390                 395                 400

Leu Ala Val Glu Arg Tyr Leu Lys Asp Gln Gln Leu Leu Gly Ile Trp
                405                 410                 415

Gly Cys Ser Gly Lys Leu Ile Cys Thr Thr Ala Val Pro Trp Asn Ala
            420                 425                 430

Ser Trp Ser Asn Lys Ser Leu Glu Gln Ile Trp Asn Asn Met Thr Trp
        435                 440                 445

Met Glu Trp Asp Arg Glu Ile Asn Asn Tyr Thr Ser Leu Ile His Ser
    450                 455                 460

Leu Ile Glu Glu Ser Gln Asn Gln Gln Glu Lys Asn Glu Gln Glu Leu
465                 470                 475                 480

Leu Glu Leu Asp Lys Trp Ala Ser Leu Trp Asn Trp Phe Asn Ile Thr
                485                 490                 495

Asn Trp Leu Trp Tyr Leu Glu His His His His His
            500                 505

<210> SEQ ID NO 8
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

```
Leu Glu Gly His Glu Val Gly Asp Lys Phe Asp Val Ala Val Gly Ala
         50                  55                  60

Asn Asp Ala Tyr Gly Gln Tyr Asp Glu Asn Leu Val Gln Arg Val Pro
 65                  70                  75                  80

Lys Asp Val Phe Met Gly Val Asp Leu Gln Val Gly Met Arg Phe
                 85                  90                  95

Leu Ala Glu Thr Asp Gln Gly Pro Val Pro Val Glu Ile Thr Ala Val
                100                 105                 110

Glu Asp Asp His Val Val Asp Gly Asn His Met Leu Ala Gly Gln
            115                 120                 125

Asn Leu Lys Phe Asn Val Glu Val Val Ala Ile Arg Glu Ala Thr Glu
130                 135                 140

Glu Glu Leu Ala His Gly His Val His Gly Ala His Asp His His
145                 150                 155                 160

Asp His Asp His Asp His His His His His
                165                 170

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Val Ala Lys Asp Leu Val Val Ser Leu Ala Tyr Gln Val Arg
 1               5                  10                  15

Thr Glu Asp Gly Val Leu Val Asp Glu Ser Pro Val Ser Ala Pro Leu
                 20                  25                  30

Asp Tyr Leu His Gly His Gly Ser Leu Ile Ser Gly Leu Glu Thr Ala
             35                  40                  45

Leu Glu Gly His Glu Val Gly Asp Lys Phe Asp Val Ala Val Gly Ala
         50                  55                  60

Asn Asp Ala Tyr Gly Ala Thr Gly His Pro Gly Ile Ile Pro Pro His
 65                  70                  75                  80

Ala Thr Leu Lys Phe Asn Val Glu Val Val Ala Ile Arg Glu Ala Thr
                 85                  90                  95

Glu Glu Glu Leu Ala His Gly His Val His Gly Ala His Asp His His
            100                 105                 110

His Asp His Asp His Asp His His His His His
             115                 120

<210> SEQ ID NO 10
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Val Gln Val Glu Thr Ile Ser Pro Gly Asp Gly Arg Thr Phe
 1               5                  10                  15

Pro Lys Arg Gly Gln Thr Cys Val Val His Tyr Thr Gly Met Leu Glu
                 20                  25                  30

Asp Gly Lys Lys Phe Asp Ser Ser Arg Asp Arg Asn Lys Pro Phe Lys
             35                  40                  45
```

```
Phe Met Leu Gly Lys Gln Glu Val Ile Arg Gly Trp Glu Glu Gly Val
         50                  55                  60

Ala Gln Met Ser Val Gly Gln Arg Ala Lys Leu Thr Ile Ser Pro Asp
 65                  70                  75                  80

Tyr Ala Tyr Gly Gln Tyr Asp Glu Asn Leu Val Gln Arg Val Pro Lys
                 85                  90                  95

Asp Val Phe Met Gly Val Asp Glu Leu Gln Val Gly Met Arg Phe Leu
                 100                 105                 110

Ala Glu Thr Asp Gln Gly Pro Val Pro Val Glu Ile Thr Ala Val Glu
            115                 120                 125

Asp Asp His Val Val Asp Gly Asn His Met Leu Ala Gly Gln Asn
    130                 135                 140

Leu Val Phe Asp Val Glu Leu Leu Lys Leu Glu His His His His
145                 150                 155                 160

His
```

<210> SEQ ID NO 11
<211> LENGTH: 332
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Gly Val Gln Val Glu Thr Ile Ser Pro Gly Asp Gly Arg Thr Phe
 1               5                  10                  15

Pro Lys Arg Gly Gln Thr Ala Val His Tyr Thr Gly Met Leu Glu
                 20                  25                  30

Asp Gly Lys Lys Phe Asp Ser Ser Arg Asp Arg Asn Lys Pro Phe Lys
            35                  40                  45

Phe Met Leu Gly Lys Gln Glu Val Ile Arg Gly Trp Glu Glu Gly Val
         50                  55                  60

Ala Gln Met Ser Val Gly Gln Arg Ala Lys Leu Thr Ile Ser Pro Asp
 65                  70                  75                  80

Tyr Ala Tyr Gly Gln Tyr Asp Glu Asn Leu Val Gln Arg Val Pro Lys
                 85                  90                  95

Asp Val Phe Met Gly Val Asp Glu Leu Gln Val Gly Met Arg Phe Leu
                 100                 105                 110

Ala Glu Thr Asp Gln Gly Pro Val Pro Val Glu Ile Thr Ala Val Glu
            115                 120                 125

Asp Asp His Val Val Asp Gly Asn His Met Leu Ala Gly Gln Asn
    130                 135                 140

Leu Val Phe Asp Val Glu Leu Leu Lys Leu Glu Gly Gly Gly Ser Gly
145                 150                 155                 160

Gly Gly Ser Gly Gly Gly Ser Gly Gly Gly Ser Gly Gly Gly Ser Gly
                165                 170                 175

Gly Gly Thr Leu Thr Val Gln Ala Arg Gln Leu Leu Ser Gly Ile Val
            180                 185                 190

Gln Gln Gln Asn Asn Glu Leu Arg Ala Ile Glu Ala Gln Gln His Leu
        195                 200                 205

Glu Gln Leu Thr Val Trp Gly Thr Lys Gln Leu Gln Ala Arg Glu Leu
    210                 215                 220

Ala Val Glu Arg Tyr Leu Lys Asp Gln Gln Leu Leu Gly Ile Trp Gly
225                 230                 235                 240

Cys Ser Gly Lys Leu Ile Cys Thr Thr Ala Val Pro Trp Asn Ala Ser
```

```
                    245                 250                 255
Trp Ser Asn Lys Ser Leu Glu Gln Ile Trp Asn Asn Met Thr Trp Met
            260                 265                 270
Glu Trp Asp Arg Glu Ile Asn Asn Tyr Thr Ser Leu Ile His Ser Leu
        275                 280                 285
Ile Glu Glu Ser Gln Asn Gln Gln Glu Lys Asn Glu Gln Glu Leu Leu
    290                 295                 300
Glu Leu Asp Lys Trp Ala Ser Leu Trp Asn Trp Phe Asn Ile Thr Asn
305                 310                 315                 320
Trp Leu Trp Tyr Leu Glu His His His His His His
                325                 330

<210> SEQ ID NO 12
<211> LENGTH: 148
<212> TYPE: PRT
<213> ORGANISM: Escherichia coli

<400> SEQUENCE: 12

Ser Glu Ser Val Gln Ser Asn Ser Ala Val Leu Val His Phe Thr Leu
  1               5                  10                  15
Lys Leu Asp Asp Gly Thr Thr Ala Glu Ser Thr Arg Asn Asn Gly Lys
               20                  25                  30
Pro Ala Leu Phe Arg Leu Gly Asp Ala Ser Leu Ser Glu Gly Leu Glu
           35                  40                  45
Gln His Leu Leu Gly Leu Lys Val Gly Asp Lys Thr Thr Phe Ser Leu
       50                  55                  60
Glu Pro Asp Ala Ala Phe Gly Val Pro Ser Pro Asp Leu Ile Gln Tyr
   65                  70                  75                  80
Phe Ser Arg Arg Glu Phe Met Asp Ala Gly Pro Glu Ile Gly Ala
               85                  90                  95
Ile Met Leu Phe Thr Ala Met Asp Gly Ser Glu Met Pro Gly Val Ile
              100                 105                 110
Arg Glu Ile Asn Gly Asp Ser Ile Thr Val Asp Phe Asn His Pro Leu
          115                 120                 125
Ala Gly Gln Thr Val His Phe Asp Ile Glu Val Leu Glu Ile Asp Pro
      130                 135                 140
Ala Leu Glu Ala
145

<210> SEQ ID NO 13
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Val Gln Val Glu Thr Ile Ser Pro Gly Asp Gly Arg Thr Phe Pro
  1               5                  10                  15
Lys Arg Gly Gln Thr Ala Val Val His Tyr Thr Gly Met Leu Glu Asp
               20                  25                  30
Gly Lys Lys Phe Asp Ser Ser Arg Asp Arg Asn Lys Pro Phe Lys Phe
           35                  40                  45
Met Leu Gly Lys Gln Glu Val Ile Arg Gly Trp Glu Glu Gly Val Ala
       50                  55                  60
Gln Met Ser Val Gly Gln Arg Ala Lys Leu Thr Ile Ser Pro Asp Tyr
   65                  70                  75                  80
```

```
Ala Tyr Gly Val Pro Ser Pro Asp Leu Ile Gln Tyr Phe Ser Arg Arg
                85                  90                  95

Glu Phe Met Asp Ala Gly Glu Pro Glu Ile Gly Ala Ile Met Leu Phe
            100                 105                 110

Thr Ala Met Asp Gly Ser Glu Met Pro Gly Val Ile Arg Glu Ile Asn
            115                 120                 125

Gly Asp Ser Ile Thr Val Asp Phe Asn His Pro Leu Ala Gly Gln Thr
        130                 135                 140

Leu Val Phe Asp Val Glu Leu Leu Lys Leu Glu His His His His His
145                 150                 155                 160

His
```

<210> SEQ ID NO 14
<211> LENGTH: 159
<212> TYPE: PRT
<213> ORGANISM: Thermococcus sp.

<400> SEQUENCE: 14

```
Met Lys Val Glu Ala Gly Asp Tyr Val Leu Phe His Tyr Val Gly Arg
  1               5                  10                  15

Phe Glu Asp Gly Glu Val Phe Asp Thr Ser Tyr Glu Ile Ala Arg
            20                  25                  30

Glu Asn Gly Ile Leu Val Glu Glu Arg Glu Tyr Gly Pro Met Trp Val
        35                  40                  45

Arg Ile Gly Val Gly Glu Ile Ile Pro Gly Leu Asp Glu Ala Ile Ile
    50                  55                  60

Gly Met Glu Ala Gly Lys Lys Thr Val Thr Val Pro Pro Glu Lys
 65                  70                  75                  80

Ala Tyr Gly Met Pro Asn Pro Glu Leu Val Ile Ser Val Pro Arg Glu
                85                  90                  95

Glu Phe Thr Lys Ala Gly Leu Gly Pro Gln Glu Gly Leu Tyr Val Met
            100                 105                 110

Thr Asp Ser Gly Ile Ala Lys Ile Val Ser Val Gly Glu Ser Glu Val
            115                 120                 125

Ser Leu Asp Phe Asn His Pro Leu Ala Gly Lys Thr Leu Val Phe Glu
        130                 135                 140

Val Glu Val Ile Glu Val Lys Lys Ala Glu Glu Asp Ser Glu Ala
145                 150                 155
```

<210> SEQ ID NO 15
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gly Val Gln Val Glu Thr Ile Ser Pro Gly Asp Gly Arg Thr Phe Pro
  1               5                  10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
```

```
            65                  70                  75                  80
Ala Tyr Gly Met Pro Asn Pro Glu Leu Val Ile Ser Val Pro Arg Glu
                    85                  90                  95

Glu Phe Thr Lys Ala Gly Leu Glu Pro Gln Glu Gly Leu Tyr Val Met
                100                 105                 110

Thr Asp Ser Gly Ile Ala Lys Ile Val Ser Val Gly Glu Ser Glu Val
                115                 120                 125

Ser Leu Asp Phe Asn His Pro Leu Ala Gly Lys Thr Leu Val Phe Asp
            130                 135                 140

Val Glu Leu Leu Lys Leu Glu His His His His His
145                 150                 155

<210> SEQ ID NO 16
<211> LENGTH: 432
<212> TYPE: PRT
<213> ORGANISM: Escherichia coli

<400> SEQUENCE: 16

Met Gln Val Ser Val Glu Thr Thr Gln Gly Leu Gly Arg Arg Val Thr
  1               5                  10                  15

Ile Thr Ile Ala Ala Asp Ser Ile Glu Thr Ala Val Lys Ser Glu Leu
                 20                  25                  30

Val Asn Val Ala Lys Lys Val Arg Ile Asp Gly Phe Arg Lys Gly Lys
             35                  40                  45

Val Pro Met Asn Ile Val Ala Gln Arg Tyr Gly Ala Ser Val Arg Gln
         50                  55                  60

Asp Val Leu Gly Asp Leu Met Ser Arg Asn Phe Ile Asp Ala Ile Ile
 65                  70                  75                  80

Lys Glu Lys Ile Asn Pro Ala Gly Ala Pro Thr Tyr Val Pro Gly Glu
                 85                  90                  95

Tyr Lys Leu Gly Glu Asp Phe Thr Tyr Ser Val Glu Phe Glu Val Tyr
                100                 105                 110

Pro Glu Val Glu Leu Gln Gly Leu Glu Ala Ile Glu Val Glu Lys Pro
            115                 120                 125

Ile Val Glu Val Thr Asp Ala Asp Val Asp Gly Met Leu Asp Thr Leu
        130                 135                 140

Arg Lys Gln Gln Ala Thr Trp Lys Glu Lys Asp Gly Ala Val Glu Ala
145                 150                 155                 160

Glu Asp Arg Val Thr Ile Asp Phe Thr Gly Ser Val Asp Gly Glu Glu
                165                 170                 175

Phe Glu Gly Gly Lys Ala Ser Asp Phe Val Leu Ala Met Gly Gln Gly
            180                 185                 190

Arg Met Ile Pro Gly Phe Glu Asp Gly Ile Lys Gly His Lys Ala Gly
        195                 200                 205

Glu Glu Phe Thr Ile Asp Val Thr Phe Pro Glu Glu Tyr His Ala Glu
    210                 215                 220

Asn Leu Lys Gly Lys Ala Ala Lys Phe Ala Ile Asn Leu Lys Lys Val
225                 230                 235                 240

Glu Glu Arg Glu Leu Pro Glu Leu Thr Ala Glu Phe Ile Lys Arg Phe
                245                 250                 255

Gly Val Glu Asp Gly Ser Val Glu Gly Leu Arg Ala Glu Val Arg Lys
            260                 265                 270

Asn Met Glu Arg Glu Leu Lys Ser Ala Ile Arg Asn Arg Val Lys Ser
        275                 280                 285

Gln Ala Ile Glu Gly Leu Val Lys Ala Asn Asp Ile Asp Val Pro Ala
```

-continued

```
                290                 295                 300
Ala Leu Ile Asp Ser Glu Ile Asp Val Leu Arg Arg Gln Ala Gln
305                 310                 315                 320

Arg Phe Gly Gly Asn Glu Lys Gln Ala Leu Glu Leu Pro Arg Glu Leu
                325                 330                 335

Phe Glu Glu Gln Ala Lys Arg Arg Val Val Gly Leu Leu Leu Gly
                340                 345                 350

Glu Val Ile Arg Thr Asn Glu Leu Lys Ala Asp Glu Arg Val Lys
                355                 360                 365

Gly Leu Ile Glu Glu Met Ala Ser Ala Tyr Glu Asp Pro Lys Glu Val
370                 375                 380

Ile Glu Phe Tyr Ser Lys Asn Lys Glu Leu Met Asp Asn Met Arg Asn
385                 390                 395                 400

Val Ala Leu Glu Glu Gln Ala Val Glu Ala Val Leu Ala Lys Ala Lys
                405                 410                 415

Val Thr Glu Lys Glu Thr Thr Phe Asn Glu Leu Met Asn Gln Gln Ala
                420                 425                 430
```

<210> SEQ ID NO 17
<211> LENGTH: 112
<212> TYPE: PRT
<213> ORGANISM: Escherichia coli

<400> SEQUENCE: 17

```
Met Leu Asp Thr Leu Arg Lys Gln Gln Ala Thr Trp Lys Glu Lys Asp
1               5                   10                  15

Gly Ala Val Glu Ala Glu Asp Arg Val Thr Ile Asp Phe Thr Gly Ser
                20                  25                  30

Val Asp Gly Glu Glu Phe Glu Gly Gly Lys Ala Ser Asp Phe Val Leu
            35                  40                  45

Ala Met Gly Gln Gly Arg Met Ile Pro Gly Phe Glu Asp Gly Ile Lys
        50                  55                  60

Gly His Lys Ala Gly Glu Glu Phe Thr Ile Asp Val Thr Phe Pro Glu
65                  70                  75                  80

Glu Tyr His Ala Glu Asn Leu Lys Gly Lys Ala Ala Lys Phe Ala Ile
                85                  90                  95

Asn Leu Lys Lys Val Glu Glu Arg Glu Leu Pro Glu Leu Thr Ala Glu
                100                 105                 110
```

<210> SEQ ID NO 18
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Leu Asp Thr Leu Arg Lys Gln Gln Ala Thr Trp Lys Glu Lys Asp
1               5                   10                  15

Gly Ala Val Glu Ala Glu Asp Arg Val Thr Ile Asp Phe Thr Gly Ser
                20                  25                  30

Val Asp Gly Glu Glu Phe Glu Gly Gly Lys Ala Ser Asp Phe Val Leu
            35                  40                  45

Ala Met Gly Gln Gly Arg Met Ile Pro Gly Phe Glu Asp Gly Ile Lys
        50                  55                  60

Gly His Lys Ala Gly Glu Glu Phe Thr Ile Asp Val Thr Phe Pro Glu
65                  70                  75                  80
```

```
Glu Tyr His Gln Tyr Asp Glu Asn Leu Val Gln Arg Val Pro Lys Asp
             85                  90                  95

Val Phe Met Gly Val Asp Glu Leu Gln Val Gly Met Arg Phe Leu Ala
            100                 105                 110

Glu Thr Asp Gln Gly Pro Val Pro Val Glu Ile Thr Ala Val Glu Asp
            115                 120                 125

Asp His Val Val Val Asp Gly Asn His Met Leu Ala Gly Gln Asn Ala
        130                 135                 140

Lys Phe Ala Ile Asn Leu Lys Lys Val Glu Glu Arg Glu Leu Pro Glu
145                 150                 155                 160

Leu Thr Ala Glu
```

<210> SEQ ID NO 19
<211> LENGTH: 270
<212> TYPE: PRT
<213> ORGANISM: Escherichia coli

<400> SEQUENCE: 19

```
Met Lys Ser Leu Phe Lys Val Thr Leu Leu Ala Thr Thr Met Ala Val
  1               5                  10                  15

Ala Leu His Ala Pro Ile Thr Phe Ala Ala Glu Ala Ala Lys Pro Ala
             20                  25                  30

Thr Ala Ala Asp Ser Lys Ala Ala Phe Lys Asn Asp Asp Gln Lys Ser
         35                  40                  45

Ala Tyr Ala Leu Gly Ala Ser Leu Gly Arg Tyr Met Glu Asn Ser Leu
     50                  55                  60

Lys Glu Gln Glu Lys Leu Gly Ile Lys Leu Asp Lys Asp Gln Leu Ile
 65                  70                  75                  80

Ala Gly Val Gln Asp Ala Phe Ala Asp Lys Ser Lys Leu Ser Asp Gln
                 85                  90                  95

Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
            115                 120                 125

Lys Glu Tyr Arg Glu Lys Phe Ala Lys Glu Lys Gly Val Lys Thr Ser
        130                 135                 140

Ser Thr Gly Leu Val Tyr Gln Val Val Glu Ala Gly Lys Gly Glu Ala
145                 150                 155                 160

Pro Lys Asp Ser Asp Thr Val Val Asn Tyr Lys Gly Thr Leu Ile
                165                 170                 175

Asp Gly Lys Glu Phe Asp Asn Ser Tyr Thr Arg Gly Glu Pro Leu Ser
            180                 185                 190

Phe Arg Leu Asp Gly Val Ile Pro Gly Trp Thr Glu Gly Leu Lys Asn
        195                 200                 205

Ile Lys Lys Gly Gly Lys Ile Lys Leu Val Ile Pro Pro Glu Leu Ala
    210                 215                 220

Tyr Gly Lys Ala Gly Val Pro Gly Ile Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
            260                 265                 270
```

<210> SEQ ID NO 20
<211> LENGTH: 114

```
<212> TYPE: PRT
<213> ORGANISM: Escherichia coli

<400> SEQUENCE: 20

Gly Leu Val Tyr Gln Val Val Glu Ala Gly Lys Gly Glu Ala Pro Lys
1               5                   10                  15

Asp Ser Asp Thr Val Val Asn Tyr Lys Gly Thr Leu Ile Asp Gly
            20                  25                  30

Lys Glu Phe Asp Asn Ser Tyr Thr Arg Gly Glu Pro Leu Ser Phe Arg
        35                  40                  45

Leu Asp Gly Val Ile Pro Gly Trp Thr Glu Gly Leu Lys Asn Ile Lys
    50                  55                  60

Lys Gly Gly Lys Ile Lys Leu Val Ile Pro Pro Glu Leu Ala Tyr Gly
65                  70                  75                  80

Lys Ala Gly Val Pro Gly Ile Pro Pro Asn Ser Thr Leu Val Phe Asp
                85                  90                  95

Val Glu Leu Leu Asp Val Lys Pro Ala Pro Leu Glu His His His His
            100                 105                 110

His His

<210> SEQ ID NO 21
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Leu Val Tyr Gln Val Val Glu Ala Gly Lys Gly Glu Ala Pro Lys
1               5                   10                  15

Asp Ser Asp Thr Val Val Asn Tyr Lys Gly Thr Leu Ile Asp Gly
            20                  25                  30

Lys Glu Phe Asp Asn Ser Tyr Thr Arg Gly Glu Pro Leu Ser Phe Arg
        35                  40                  45

Leu Asp Gly Val Ile Pro Gly Trp Thr Glu Gly Leu Lys Asn Ile Lys
    50                  55                  60

Lys Gly Gly Lys Ile Lys Leu Val Ile Pro Pro Glu Leu Ala Tyr Gly
65                  70                  75                  80

Gln Tyr Asp Glu Asn Leu Val Gln Arg Val Pro Lys Asp Val Phe Met
                85                  90                  95

Gly Val Asp Glu Leu Gln Val Gly Met Arg Phe Leu Ala Glu Thr Asp
            100                 105                 110

Gln Gly Pro Val Pro Val Glu Ile Thr Ala Val Glu Asp His Val
        115                 120                 125

Val Val Asp Gly Asn His Met Leu Ala Gly Gln Asn Leu Val Phe Asp
    130                 135                 140

Val Glu Leu Leu Asp Val Lys Pro Ala Pro Leu Glu His His His His
145                 150                 155                 160

His His

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 22

Gly Gly Gly Ser Gly Gly Gly Ser Gly Gly Gly Ser Gly Gly Gly Ser
 1               5                  10                  15
Gly Gly Gly Ser Gly Gly Gly
            20

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

His Asp His Asp His Asp His Asp His His His His His His
 1               5                  10

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 24

His His His His His His
 1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Gly Ser Gly Gly Gly Ser Gly Gly
 1               5                  10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Gly His Asp His Asp His Asp His His His His His His
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Gly Ser Gly Gly Gly Ser Gly Gly Gly
 1               5                  10
```

FUSION PROTEIN COMPRISING AN *E. COLI* CHAPERONE PROTEIN AND A HUMAN CHAPERONE PROTEIN

RELATED APPLICATIONS

This application is a continuation of PCT/EP2006/012599 filed Dec. 29, 2006 and claims priority to EP 06000056.9 filed Jan. 3, 2006 and to EP 06009106.3 filed May 3, 2006.

FIELD OF THE INVENTION

The present invention relates to the cloning, expression and uses of a chimeric fusion protein with superior chaperone and folding activities compared to the naturally occurring counterparts. This invention relates to a chimeric fusion protein encoded by a recombinant DNA molecule comprising nucleotide sequences coding for a polypeptide binding segment of a non-human chaperone protein and nucleotide sequences coding for an FK506 binding protein (FKBP) or an FK506-binding-protein-like domain (FKBP-like domain). In particular, this invention relates to a chimeric fusion protein encoded by a recombinant DNA molecule comprising nucleotide sequences coding for a polypeptide binding segment of a non-human chaperone protein and nucleotide sequences coding for a human FKBP type peptidyl-prolyl-cis/trans isomerase (PPIase), methods of producing these chimeric fusion proteins and their uses as folding helpers in the production of other proteins and for immunization of laboratory animals and in the process of the production of vaccines or pharmaceuticals, their use as a fusion module in recombinant protein technology and as folding helpers for performing immunoassays.

BACKGROUND

Nowadays molecular chaperones play an important role in a wide range of biotechnological applications (Mogk et al. 2002 Chembiochem 3, 807). There are a lot of folding helpers which possess chaperone as well as enzymatic properties. For these reasons they are useful for a variety of practical applications in the field of protein folding.

Chaperones, which are known as classical "folding helpers", are polypeptides that assist the folding and maintenance of structural integrity of other proteins. They possess the ability to promote the folding of a polypeptide both in vivo and in vitro. Generally, folding helpers are subdivided into folding catalysts and chaperones. Folding catalysts accelerate the rate limiting steps in protein folding due to their catalytic function. Examples of catalysts are further described below. Chaperones are known to bind to denatured, partially denatured, or hydrophobic surfaces of polypeptides and thus help to re-nature proteins or to keep them in solution. Thus, unlike folding catalysts, chaperones exert a mere binding function (Buchner, J., Faseb J 10 (1996) 10-19). Chaperones are ubiquitous stress-induced proteins involved in protein maturation, folding, translocation, and degradation (Gething, M. J. and Sambrook, J., Nature 355 (1992) 33-45). Although also present under normal growth conditions, they are abundantly induced under stress conditions. This further supports the idea that their physiological function is to cope with stress conditions.

To date, several different families of chaperones are known. All these chaperones are characterized by their ability to bind unfolded or partially unfolded proteins and have a physiological function that is linked to the correct folding of proteins or the removal of denatured or aggregated protein.

Well-characterized examples of chaperones are members of the so-called heat-shock families of proteins, which are designated according to their relative molecular weight, for example, hsp100, hsp90, hsp70, and hsp60, as well as the so-called shsps (small heat-shock-proteins) as described by Buchner, J., Faseb J 10 (1996) 10-19, and by Beissinger, M. and Buchner, J., Biol. Chem. 379 (1998) 245-59.

Folding catalysts, unlike chaperones, assist folding by accelerating defined rate-limiting steps, thereby reducing the concentration of aggregation-prone folding intermediates. One class of catalysts, the protein disulfide isomerases (alternatively designated as thiol-disulfide-oxido-reductases), catalyzes the formation or the rearrangement of disulfide bonds in secretory proteins. In gram-negative bacteria, the oxidative folding of secretory proteins in the periplasm is adjusted by a cascade of protein disulfide isomerases designated DsbA, DsbB, DsbC, and DsbD (Bardwell, J. C., Mol Microbiol 14 (1994) 199-205 and Missiakas, D., et al., Embo J 14 (1995) 3415-24).

Another important class of folding catalysts referred to as peptidyl prolyl cis/trans isomerases (PPIs) comprise different members such as CypA, PpiD (Dartigalongue, C. and Raina, S., Embo J 17 (1998) 3968-80, FkpA (Danese, P. N., et al., Genes Dev 9 (1995) 387-98), trigger factor (Crooke, E., and Wickner, W., Proc Natl Acad Sci USA 84 (1987) 5216-20 and Stoller, G., et al., Embo J 14 (1995) 4939-48), and SlyD (Hottenrott, S., et al., J Biol Chem 272 (1997) 15697-701).

Due to sequence similarity and protein topology, prolyl isomerases are divided into three distinct families, the cyclophilins, the FK506 binding proteins (FKBPs), and the parvulins. Cyclophilins bind to and are inhibited by the immunosuppressant cyclosporin A. Parvulins are a family of prolyl isomerases, which are inhibited neither by cyclosporin A nor by FK506. FKBPs bind to and are inhibited by FK506 and rapamycin. (The acronym FKBP stands for "FK506-binding protein." FK506 is a macrolide that is used as immunosuppressant drug). The first x-ray structure of an FKBP to be determined at high resolution was that of human FKBP12. It is a five-stranded antiparallel β-sheet wrapping with a right-handed twist around a short α-helix. The five-stranded β-sheet framework includes residues 2 to 8, 21 to 30, 35 to 38 with 46 to 49, 71 to 76, and 97 to 106 (van Duyne et al., Science (1991) 252, 839-842). Subsequent research has shown that FKBPs, as well as cyclophilins and parvulins, form a highly conserved family of enzymes found in a wide variety of procaryotic and eucaryotic organisms (for review see John E. Kay, Biochem. J. (1996) 314, 361-385). For instance, 10 prolyl isomerases have been identified in *E. coli* so far (2 parvulins, 3 cyclophilins and 5 FKBPs).

Usually, FKBPs are defined according to the binding criterion, i.e., they recognize and bind FK506 with high affinity in the nanomolar range. There are, however, FKBP-like domains, which are no more susceptible to prolyl isomerase inhibition by FK506. These FKBP-like domains share significant sequence similarity with FKBP12, but some of the amino acid residues mediating FK506 binding are mutated, and the affinity is shifted to the micromolar range. For instance, SlyD and trigger factor (two cytosolic PPIases from the *E. coli* cytosol) may be envisaged as FKBP-like proteins. Both prolyl isomerases harbor domains sharing significant sequence homology with FKBP12, but their binding affinity to FK506 is rather poor and lies in the micromolar range (Scholz et al. Biochemistry (2006) 45, 20-33). In terms of sequence similarity and protein topology, however, both SlyD and trigger factor are undoubtedly members of the FKBP family (Wülfing et al., J. Biol. Chem (1994) 269(4) 2895-2901, Callebaut & Mornon. FEBS Lett. (1995) 374(2), 211-215).

FKBP domains and FKBP-like domains may form part of larger molecules with complex topologies. In mammalian cells, FKBP12, FKBP12A, and FKBP13 contain only the basic FKBP domain, while FKBP25 and FKBP52 have one or more FKBP domains as part of a larger molecule (for review see John E. Kay, Biochem. J. (1996) 314, 361-385).

Modularly constructed FKBPs are also found in procaryotic cells, for example, the aforementioned trigger factor consists of three well-separated domains with distinct functions. The N-domain mediates binding to the 50S subunit of the E. coli ribosome (Hesterkamp et al., J Biol Chem. (1997) Aug. 29; 272(35):21865-71). The M (middle) domain harbors the prolyl isomerase active site (Stoller et al., FEBS Lett. 1996 Apr. 15; 384(2):117-22), and the C domain encompasses the polypeptide binding site which mediates binding of extended polypeptide substrates (Merz et al., J Biol Chem. 2006 Oct. 20; 281 (42) 31963-31971). Another example of a modularly constructed peptidyl-prolyl isomerase is the periplasmic FkpA, which consists of an N-terminal chaperone and dimerization domain and a C-terminal FKBP domain (Saul et al., J. Mol. Biol (2004) 335, 595-608).

Some folding helpers comprise both a catalytically active domain as well as a chaperone (or polypeptide binding) domain. For example, the prolyl-isomerases trigger factor (Scholz et al. 1997, Embo J. 16, 54-58; Zarnt et al. 1997, JMB 271, 827-837), FkpA (Saul et al. 2004. JMB 335, 595-608), and SlyD belong to these folding helpers. Recently it could be shown that FkpA and SlyD are remarkably suitable as fusion modules for the production of recombinant proteins. Both chaperones increase the expression rate of their client proteins, support correct refolding and increase the solubility of aggregation-prone proteins like retroviral surface proteins (Scholz et al. 2005, JMB 345, 1229-1241 and WO 03/000877).

FkpA, SlyD, and SlpA are bacterial chaperones that belong to the family of FK506 binding proteins. As mentioned above, FK506 is a macrolide that is used as immunosuppressant drug. The cellular receptors for FK506 are still in the focus of world wide research groups. At the beginning of the 1990s, the three-dimensional structure of a human FKBP, i.e., FKBP12, could be resolved (van Duyne et al. 1991, Science 252, 839-842). In contrast to FkpA, SlyD, and SlpA, the human FKPB12 does not have any chaperone activity, and it only has a modest prolyl isomerase activity.

In many diagnostic applications recombinantly produced proteins are used, e.g., as antigens. These antigens may be produced as fusion proteins containing one part that makes up the antigenic portion or target polypeptide which has to be recognized by a specific binding partner that is present in the sample or in the assay mixture. The oilier part of the recombinantly produced fusion protein is a polypeptide portion that is fused to the antigenic part in order to facilitate the cloning, expression, folding, solubilization or purification of the specific antigen. The synthesis of recombinantly produced fusion proteins is well described in prior art. It is quite common to use chaperones as that part of the fusion protein that functions as a helping molecule for the expression, folding, purification, and solubilization of the target polypeptide. For example, U.S. Pat. No. 6,207,420 discloses a fusion protein system for the expression of heterologous proteins, i.e., the amino acid sequences of the target polypeptides part and the fused peptide part originate from different organisms. WO 03/000878 describes the use of FKBP chaperones as tools for the expression of retroviral surface glycoproteins.

While common methods for the expression, purification, folding and solubilization of fusion proteins seem to work reliably, in particular those methods in which folding helpers are used, there still remain some problems to be solved. For instance, whenever a fusion protein containing non-human amino acid sequences is used as a binding partner in a human diagnostic test, there is still a problem of interferences due to these non-human proteins used. Quite often antibodies that abundantly occur in human blood samples react with bacterial proteins present in the assay reagents. Such interferences may result in high background noise or may even cause wrong test results. Another common problem consists in adapting or optimizing the affinity of the fusion partner to the respective client protein. The affinity of any fusion module for the target part must be well balanced. If the affinity is too high, the fusion protein will be perfectly soluble, but the complex between fusion module and client protein will remain in a closed conformation and will thus be inactive in an immunological assay. If the affinity is too low, the client protein should be accessible and active in an immunoassay, but it will not be sufficiently protected against aggregation.

It was therefore an object of the present invention to provide an expression system that is suitable for producing chaperone-like proteins that may be used in a wide range of biotechnological and in particular in diagnostic and pharmaceutical applications which cause no or only little interferences with molecules and substances present in isolated human samples. The prior art does not disclose an effective folding helper, i.e., a helper that exerts both high catalytic and chaperone activities, that consists mainly of human amino acid sequences.

Although several protein sequence alignments of human and bacterial chaperones exist (Wülfing et al 1994, JBC 269, 2895-2901; Hottenrott et al. 1997, JBC 272, 15697-15701; Suzuki et al. 2003. JMB 328, 1149-1160), if has not yet been shown how an efficient humanized folding helper having dual function, i.e., catalytic and chaperone-like functions, may be generated.

SUMMARY OF THE INVENTION

Surprisingly, we have been able to show that by fusing the polypeptide binding segment of a non-human chaperone protein to sequences that originate from, an FK506 binding protein (FKBP) or an FKBP-like domain (FK506-binding-protein-like domain), molecules with superior folding helper activities may be produced.

In particular, by fusing the polypeptide binding segment of a non-human chaperone protein to sequences that originate from a human peptidyl-prolyl-cis/trans isomerase (PPIase) of the FKBP type, we can generate a humanized PPIase chaperone molecule with folding helper activities superior to those of the wild type folding helpers. These chimeric humanized folding helpers represent extremely promising tools for producing native-like folded protein reagents for a wide range of biotechnological applications since they may cause no or only little interference when used in diagnostic tests or pharmaceutical applications and since their chaperone properties may be tailored for the respective protein.

Preferred ways of designing recombinant DNA molecules coding for such a chimeric fusion protein as well as their use as part of an expression vector, a host cell comprising such an expression vector, and in the production of a chimeric fusion protein are also disclosed.

Also the recombinantly produced chimeric fusion proteins themselves that exhibit surprising and advantageous properties in particular with regard to their catalytic efficiencies are part of the invention.

In further embodiments the uses of the recombinantly produced fusion proteins as a folding helper for target proteins, as a folding helper in the process of production of target proteins, as an additive to an immunoassay mixture, in the process of production of a vaccine, for immunization of laboratory animals and in the process of producing pharmaceuticals are disclosed.

In addition a composition comprising a recombinantly produced chimeric fusion protein and a pharmaceutically acceptable excipient is disclosed.

BRIEF DESCRIPTION OF THE SEQUENCE LISTING

The sequence listing attached contains the SEQ ID NOs as follows:

SEQ ID NO: 1 represents the *E. coli* SlyD amino acid sequence according to Suzuki et al. 2003. JMB 328, 1149-1160 which is also accessible via ID P0A9K9 of the SwissProt database.

```
MKVAKDLVVS LAYQVRTEDG VLVDESPVSA PLDYLHGHGS

LISGLETALE GHEVGDKFDV AVGANDAYGQ YDENLVQRVP

KDVFMGVDEL QVGMRFLAET DQGPVPVEIT AVEDDHVVVD

GNHMLAGQNL KFNVEVVAIR EATEEELAHG HVHGAHDHHH

DHDHDGCCGG HGHDHGHEHG GEGCCGGKGN GGCGCH
```

SEQ ID NO: 2 shows the human FKBP12 amino acid sequence (Suzuki et al. supra) which is also accessible via ID P62942 of the SwissProt database.

```
GVQVETISPG DGRTFPKRGQ TCVVHYTGML EDGKKFDSSR

DRNKPFKFML GKQEVIRGWE EGVAQMSVGQ RAKLTISPDY

AYGATGHPGI IPPHATLVFD VELLKLE
```

SEQ ID NO: 3 shows the human FKBP12 amino acid sequence as shown in SEQ ID NO: 2 which carries a mutation in position no. 22. To achieve a better solubility cysteine 22 has been changed to alanine (C22A). In addition a C-terminal hexa-histidine tag (SEQ ID NO: 24) has been added.

```
GVQVETISPG DGRTFPKRGQ TAVVHYTGML EDGKKFDSSR

DRNKPFKFML GKQEVIRGWE EGVAQMSVGQ RAKLTISPDY

AYGATGHPGI IPPHATLVFD VELLKLEHHH HHH
```

SEQ ID NO: 4 shows the amino acid sequence of a preferred chimeric folding helper protein FKBP12-IF1 according to the invention. The SlyD insert is underlined.

```
FKBP12 G1-G83/SlyD Q70-N129/FKBP12 L97-E107

GVQVETISPG DGRTFPKRGQ TCVVHYTGML EDGKKFDSSR

DRNKPFKFML GKQEVIRGWE EGVAQMSVGQ RAKLTISPDY

AYGQYDENLV QRVPKDVFMG VDELQVGMRF LAETDQGPVP

VEITAVEDDH VVVDGNHMLA GQNLVFDVEL LKLE
```

SEQ ID NO: 5 shows the amino acid sequence of a preferred chimeric folding helper protein FKBP12-IF1 according to the invention. The SlyD insert is underlined. The sequence corresponds to SEQ ID NO: 4, but cysteine 22 has been replaced by alanine.

```
FKBP12 G1-683/SlyD Q70-N129/FKBP12 L97-E107

GVQVETISPG DGRTFPKRGQ TAVVHYTGML EDGKKFDSSR

DRNKPFKFML GKQEVIRGWE EGVAQMSVGQ RAKLTISPDY

AYGQYDENLV QRVPKDVFMG VDELQVGMRF LAETDQGPVP

VEITAVEDDH VVVDGNHMLA GQNLVFDVEL LKLE
```

Figure 8:
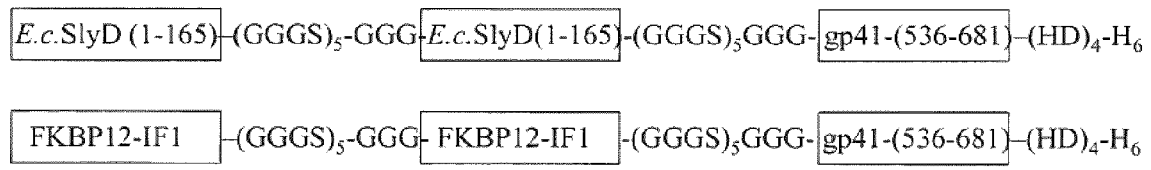
FIG. 8: Schematic figure of the fusion proteins SlyD*-SlyD*-gp41 and hFKBP12-IF1-hFKBP12-IF1-gp41. Both the fusion modules and gp41 are highlighted with boxes. The chaperone modules SlyD* and hFKBP12-IF1 are connected with the respective target molecule by a flexible, 23 amino acid linker rich in glycine and serine residues. The hexahistidine tag (SEQ ID NO: 24) is fused to the C-terminus of the target molecule via a spacer segment, which improves accessibility and facilitates both purification and refolding. The linker (SEQ ID NO: 22) consists of five iterative GGGS (Residues 1-5 of SEQ ID NO: 22) elements (G: glycine, S: serine), the spacer (SEQ ID NO: 23) comprises four HD repeats (H: histidine, D: aspartic acid) that naturally occur in the unstructured C-terminal tail of SlyD.

SEQ ID NO: 6 shows the amino acid sequence of the fusion protein SlyD*-SlyD*-gp41 with an HIV-1 gp41 polypeptide as target polypeptide fused to two SlyD* units (comparison to state of the art). A schematic drawing of the fusion proteins of the type Carrier-Carrier-Target is shown in FIG. 8; see also Example 1.

EcSlyD-[GGGS]$_5$GGG-EcSlyD-[GGGS]$_5$GGG-gp41 (536-681; L555E, L566E, I573T, I580E)-HGHDHDHD-His6, pET24a (The "[GGGS]$_5$GGG" linker is disclosed as SEQ ID NO: 22 and HG[HD]$_4$H$_6$ is disclosed as SEQ ID NO: 26.)

```
MKVAKDLVVS LAYQVRTEDG VLVDESPVSA PLDYLHGHGS

LISGLETALE GHEVGDKFDV AVGANDAYGQ YDENLVQRVP

KDVFMGVDEL QVGMRFLAET DQGPVPVEIT AVEDDHVVVD

GNHMLAGQNL KFNVEVVAIR EATEEELAHG HVHGAHDHHH

DHDHDGGGSG GGSGGGSGGG SGGGSGGGKV AKDLVVSLAY

QVRTEDGVLV DESPVSAPLD YLHGHGSLIS GLETALEGHE

VGDKFDVAVG ANDAYGQYDE NLVQRVPKDV FMGVDELQVG

MRFLAETDQG PVPVEITAVE DDHVVVDGNH MLAGQNLKFN

VEVVAIREAT EEELAHGHVH GAHDHHHDHD NDGGGSGGGS

GGGSGGGSGG GSGGGTLTVQ ARQLLSGIVQ QQNNELRAIE

AQQHLEQLTV WGTKQLQARE LAVERYLKDQ QLLGIWGCSG

KLICTTAVPW NASWSNKSLE QIWNNMTWME WDREINNYTS

LIHSLIEESQ NQQEKNEQEL LELDKWASLW NWFNITNWLW

YHGHDHDHDH HHHHH
```

SEQ ID NO: 7 shows the amino acid sequence of the chimeric fusion protein hFKBP12-IF1-hFKBP12-IF1-gp41 with an HIV-1 gp41 polypeptide as target polypeptide fused to hFKBP12-IF1 according to the invention (tandem fusion protein). A schematic drawing of this protein is shown in FIG. 8; see also Example 1.

```
MGVQVETISP GDGRTFPKRG QTAVVHYTGM LEDGKKFDSS

RDRNKPFKFM LGKQEVIRGW EEGVAQMSVG QRAKLTISPD
```

-continued

```
YAYGQYDENL VQRVPKDVFM GVDELQVGNR FLAETDQGPV

PVEITAVEDD HVVVDGNHML AGQNLVFDVE LLKLEGGGSG

GGSGGGSGGG SGGGSGGGGV QVETISPGDG RTFPKRGQTA

VVHYTGMLED GKKFDSSRDR NKPFKFMLGK QEVIRGWEEG

VAQMSVGQRA KLTISPDYAY GQYDENLVQR VPKDVFMGVD

ELQVGMRFLA ETDQGPVPVE ITAVEDDHVV VDGNHMLAGQ

NLVFDVELLK LEGGGSGGGS GGGSGGGSGG GSGGGTLTVQ

ARQLLSGIVQ QQNNELRAIE AQOHLEQLTV WGTKQLQARE

LAVERYLKDQ QLLGIWGCSG KLICTTAVPW NASWSNKSLE

QIWNNMTWME WDREINNYTS LIHSLIEESQ NQQEKNEQEL

LELDKWASLW NWFNITNWLW YLEHHHHHH
```

SEQ ID NO: 8 shows the amino acid sequence of SlyD* (SlyD 1-165)—which corresponds to SEQ ID NO: 1, but is C-terminally truncated after residue no. D165 (aspartic acid). In addition SEQ ID NO: 8 carries a hexa-histidine tag (SEQ ID NO: 24) at its C-terminal end.

```
MKVAKDLVVS LAYQVRTEDG VLVDESPVSA PLDYLHGHGS

LISGLETALE GHEVGDKFDV AVGANDAYGQ YDENLVQRVP

KDVFMGVDEL QVGMRFLAET DQGPVPVEIT AVEDDHVVVD

GNHMLAGQNL KFNVEVVAIR EATEEELAHG HVHGAHDHHH

DHDHDHHHHH H
```

SEQ ID NO: 9 shows the amino acid sequence of SlyD* (1-165) as shown in SEQ ID NO: 8 without IF-loop. This variant is also called SlyD* ΔIF-loop. For refolding and purification, it carries a hexa-histidine tag (SEQ ID NO: 24) at its C-terminus.

```
MKVAKDLVVS LAYQVRTEDG VLVDESPVSA PLDYLHGHGS

LISGLETALE GHEVGDKFDV AVGANDAYGA TGHPGIIPPH

ATLKFNVEVV AIREATEEEL AHGHVHGAHD HHHDHDHDHH

HHH
```

SEQ ID NO: 10 shows the amino acid sequence of a synthetic gene encoding the protein FKBP12-IF1 with a C-terminal hexa-histidine tag (SEQ ID NO: 24) to facilitate purification. The N-terminal methionine is cleaved off after translation by the bacterial N-methionyl-aminopeptidase, so the mature polypeptide actually starts with glycine 1. When cysteine 22 is replaced by alanine, the resulting amino acid sequence for FKBP12-IF1 corresponds to SEQ ID NO: 5.

```
MGVQVETISP GDGRTFPKRG QTCVVHYTGM LEDGKKFDSS

RDRNKPFKFM LGKQEVIRGW EEGVAQMSVG QRAKLTISPD

YAYGQYDENL VQRVPKDVFM GVDELQVGMR FLAETDQGPV

PVEITAVEDD HVVVDGNHML AGQNLVFDVE LLKLEHHHHH

H
```

SEQ ID NO: 11 shows the FKBP12-IF1(C22A)-gp41 fusion construct (see also Example 1).

```
MGVQVETISP GDGRTFPKRG QTAVVHYTGM LEDGKKFDSS

RDRNKPFKFM LGKQEVIRGW EEGVAQNSVG QRAKLTISPD

YAYGQYDENL VQRVPKDVFM GVDELQVGMR FLAETDQGPV

PVEITAVEDD HVVVDGNHML AGQNLVFDVE LLKLEGGGSG

GGSGGGSGGG SGGGSGGGTL TVQARQLLSG IVQQQNNELR

AIEAQQHLEQ LTVWGTKQLQ ARELAVERYL KDQQLLGIWG

CSGKLICTTA VPWNASWSNK SLEQIWNNMT WMEWDREINN

YTSLIHSLIE ESQNQQEKNE QELLELDKWA SLWNWFNITN

WLWYLEHHHH HH
```

SEQ ID NO: 12 shows the *E. coli* SlpA amino acid sequence according to Suzuki et al. 2003, JMB 328, 1149-1160 which is also accessible via ID P0AEM0 of the SwissProt database. The N-terminal Met residue which is present in the unprocessed protein (not shown in SEQ ID NO: 12) is removed post-translationally. Hitherto, information on SlpA has been very scarce. Apart from a preliminary characterization as a prolyl isomerase with a rather low activity towards peptide substrates, virtually nothing has been known on SlpA so far.

```
SESVQSNSAV LVHFTLKLDD GTTAESTRNN GKPALFRLGD

ASLSEGLEQH LLGLKVGDKT TFSLEPDAAF GVPSPDLIQY

FSRREFMDAG EPEIGAIMLF TAMDGSEMPG VIREINGDSI

TVDFNHPLAG QTVHFDIEVL EIDPALEA
```

SEQ ID NO: 13 shows the amino acid sequence of a further preferred chimeric folding helper protein FKBP12-IF4 according to the invention. The SlpA insert is underlined. In addition a C-terminal hexa-histidine tag (SEQ ID NO: 24) has been added.

```
FKBP12 G1-G83/SlpA V72-T132/FKBP12 L97-E107

GVQVETISPG DGRTFPKRGQ TAVVHYTGML EDGKKFDSSR

DRNKPFKFML GKQEVIRGWE EGVAQMSVGQ RAKLTISPDY

AYGVPSPDLI QYFSRREFMD AGEPEIGAIM LFTAMDGSEM

PGVIREINGD SITVDFNHPL AGQTLVFDVE LLKLEHHHHH

H
```

SEQ ID NO: 14 shows the *Thermococcus* FKBP18 amino acid sequence which is also accessible via ID O93778 of the SwissProt database.

```
MKVEAGDYVL FHYVGRFEDG EVFDTSYEEI ARENGILVEE

REYGPMWVRI GVEIIPGLD EAIIGMEAGE KKTVTVPPEK

AYGMPNPELV ISVPREEFTK AGLEPQEGLY VMTDSGIAKI

VSVGESEVSL DFNHPLAGKT LVFEVEVIEV KKAEEDSEA
```

SEQ ID NO: 15 shows the amino acid sequence of a further preferred chimeric folding helper protein FKBP12-IF5 according to the invention. The *Thermococcus* FKBP18 insert is underlined. In addition a C-terminal hexa-histidine tag (SEQ ED NO: 24) has been added.

```
FKBP12 G1-G83/TcFKBP18 M84-T140/FKBP12 L97-E107
GVQVETISPG DGRTFPKRGQ TCVVHYTGML EDGKKFDSSR
DRNKPFKFML GKQEVIRGWE EGVAQMSVGQ RAKLTISPDY
AYGMPNPELV ISVPREEFTK AGLEPQEGLY VMTDSGIAKI
VSVGESEVSL DFNHPLAGKT LVFDVELLKL EHHHHHH
```

SEQ ID NO: 16 shows the *Escherichia coli* trigger factor amino acid sequence which is also accessible via ID P0A850 of the SwissProt database.

```
MQVSVETTQG LGRRVTITIA ADSIETAVKS ELVNVAKKVR
IDGFRKGKVP MNIVAQRYGA SVRQDVLGDL MSRNFIDAII
KEKINPAGAP TYVPGEYKLG EDFTYSVEFE VYPEVELQGL
EAIEVEKPIV EVTDADVDGM LDTLRKQQAT WKEKDGAVEA
EDRVTIDFTG SVDGEEFEGG KASDFVLAMG QGRMIPGFED
GIKGHKAGEE FTIDVTFPEE YHAENLKGKA AKFAINLKKV
EERELPELTA EFIKRFGVED GSVEGLRAEV RKNMERELKS
AIRNRVKSQA IEGLVKANDI DVPAALIDSE IDVLRRQAAQ
RFGGNEKQAL ELPRELFEEQ AKRRVVGLL LGEVIRTNEL
KADEERVKGL IEEMASAYED PKEVIEFYSK NKELMDNMRN
VALEEQAVEA VLAKAKVTEK ETTFNELMNQ QA
```

SEQ ID NO: 17 shows the FKBP domain of the *E. coli* trigger factor according to SEQ ID NO: 16. Amino acids methionine 140 to glutamic acid 251 belong to the FKBP domain of the trigger factor.

```
MLDTLRKQQA TWKEKDGAVE AEDRVTIDFT GSVDGEEFEG
GKASDFVLAM GQGRMIPGFE DGIKGHKAGE EFTIDVTFPE
EYHAENLKGK AAKFAINLKK VEERELPELT AE
```

SEQ ID NO: 18 shows the amino acid sequence of a further embodiment of the invention. In this chimeric folding helper protein (trigger factor-IF/SlyD) the IF domain originating from SlyD is inserted into the FKBP domain of the *E. coli* trigger factor. The SlyD insert is underlined.
*E. coli* Trigger Factor/FKBP-Domäne+IF

```
TF M140-H222/SlyD Q70-N129/TF A231-E251
MLDTLRKQQA TWKEKDGAVE AEDRVTIDFT GSVDGEEFEG
GKASDFVLAM GQGRMIPGFE DGIKGHKAGE EFTIDVTFPE
EYHQYDENLV QRVPKDVFMG VDELQVGMRF LAETDQGPVP
VEITAVEDDH VVVDGNHMLA GQNAKFAINL KKVEERELPE
LTAE
```

SEQ ID NO: 19 shows the amino acid sequence of the unprocessed precursor of FkpA from *E. coli*. Newly translated FkpA carries an N-terminal signal sequence. (Met 1-Ala 25) for the export into the periplasm. After passage of the inner membrane a signal peptidase specifically removes the signal sequence so that this sequence is missing in the processed functional protein. FkpA comprises an N-terminal chaperone and dimerization domain and a C-terminal isomerase domain (Gly 147-K249). In the RNaseT1 test FkpA shows a catalytic efficiency of about 250,000 $M^{-1}s^{-1}$. The FkpA sequence is also accessible via SwissProt ID: P45523.

```
MKSLFKVTLDL ATTMAVALHA PITFAAEAAK PATAADSKAA
FKNDDQKSAY ALGASLGRYM ENSLKEQEKL GIKLDKDQLI
AGVQDAFADK SKLSDQEIEQ TLQAFEARVK SSAQAKMEKD
AADNEAKGKE YREKFAKEKG VKTSSTGLVY QVVEAGKGEA
PKDSDTVVVN YKGTLIDGKE FDNSYTRGEP LSFRLDGVIP
GWTEGLKNIK KGGKIKLVIP PELAYGKAGV PGIPPNSTLV
FDVELLDVKP APKADAKPEA DAKAADSAKK
```

SEQ ID NO: 20 shows the amino acid sequence of the FKBP domain of FkpA as shown in SEQ ID NO: 19 (G147-K249). The C-terminal sequence LE is contained for reasons of cloning strategy. A C-terminal hexa-histidine tag (SEQ ID NO: 24) has been added to facilitate purification. This FKBP domain is assumed to have a weak activity in the RNaseT1 folding test, the activity ranging between SlyD* ΔIF loop and human FKBP12 (see table 1).

```
GLVYQVVEAG KGEAPKDSDT VVVNYKGTLI DGKEFDNSYT
RGEPLSFRLD GVIPGWTEGL KNIKKGGKIK LVIPPELAYG
KAGVPGIPPN STLVFDVELL DVKPAPLEHH HHHH
```

SEQ ID NO: 21 shows the amino acid sequence of a further embodiment according to the invention. In the chimeric folding helper protein FkpA-IF/SlyD the IF domain originating from SlyD is inserted into the FKBP domain of FkpA (as shown in SEQ ID NO: 20). A C-terminal hexa-histidine tag (SEQ ID NO: 24) has been added to facilitate purification. This chimeric folding helper protein is expected to show a high activity in the RNaseT1 folding test.

```
FkpA G147-G226/SlyD Q70-N129/FkpA L239-P252
GLVYQVVEAG KGEAPKDSDT VVVNYKCTLI DGKEFDNSYT
RGEPLSFRLD GVIPGWTEGL KNIKKGGKIK LVIPPELAYG
QYDENLVQRV PKDVFMGVDE LQVGMRFLAE TDQGPVPVEI
TAVEDDHVVV DGNHMLAGQN LVFDVELLDV KPAPLEHHHH
HH
```

DETAILED DESCRIPTION OF THE INVENTION

The present invention relates to a recombinant DNA molecule encoding a chimeric fusion protein comprising
  a) at least one nucleotide sequence coding for a polypeptide binding segment of a non-human chaperone protein,
  b) upstream thereto at least one nucleotide sequence coding for an FK506 binding protein (FKBP) or an FK506-binding-protein-like domain (FKBP-like domain), and c) downstream thereto at least one nucleotide sequence coding for an FK506 binding protein (FKBP) or an FK506-binding-protein-like domain (FKBP-like domain).

The nucleotide sequences of a) on the one hand and b) and c) on the other hand may stem from the same organism, but they must encode distinct parent FKBP molecules. More precisely, a) encodes the chaperone domain of one FKBP molecule (e.g., SlyD or SlpA), and b) and c) encode the FKBP domain or the FKBP-like domain of another molecule (e.g., human FKBP12). The nucleotide sequences coding for an FK506 binding protein (FKBP) or an FK506-binding-protein-like domain (FKBP-like domain), i.e., those of part b) and part c), may originate from the same organism, but they may also originate from different organisms. Preferably the sequences given under b) and c) originate from the same organism. More preferably, they originate from the same parent FKBP molecule like, for example, human FKBP12.

In particular, the present invention relates to a recombinant DNA molecule encoding a chimeric fusion protein comprising
a) at least one nucleotide sequence coding for a polypeptide binding segment of a non-human chaperone protein,
b) upstream thereto at least one nucleotide sequence encoding an FKBP type human peptidyl-prolyl-cis/trans isomerase (PPIase), and
c) downstream thereto at least one nucleotide sequence encoding an FKBP type human peptidyl-prolyl-cis/trans isomerase (PPIase).

The term "recombinant DNA molecule" refers to a DNA molecule which is made by the combination of two otherwise separated segments of sequence accomplished by the artificial manipulation of isolated segments of polynucleotides by genetic engineering techniques or by chemical synthesis. In so doing, one may join together polynucleotide segments of desired functions to generate a desired combination of functions.

The term "chimeric fusion protein" means that the polypeptide binding domain and the FKBP (or FKBP-like) domain stem from different parent molecules. We consider the FKBP or FKBP-like domain to be a folding scaffold onto which the chaperone domain can be grafted, yielding a super chaperone with superior folding helper activities. In the current invention, a non-human polypeptide is fused to human polypeptide sequences. A chimeric protein may also be called a "mosaic protein". Since one object of the current invention is to humanize a folding helper protein so that the resulting protein becomes more tolerable in diagnostic applications, the percentage of the non-human amino acid sequences preferably does not exceed a portion of 50 percent compared to the length of the complete chimeric fusion protein.

Preferably the nucleotide sequences according to a), b), and c) are not separated by additional linker sequences but are directly adjacent to one another.

"Upstream" direction means that the nucleotide is located in 5' direction of the polynucleotide, i.e., towards the first nucleotide. In terms of amino acid sequence, the term "upstream" means that the amino acid is located in N-terminal direction, i.e., towards the start of the polypeptide.

"Downstream" direction means that the nucleotide is located in 3' direction of the polynucleotide, i.e., towards the last nucleotide. In terms of amino acid sequence, the term "downstream" means that the amino acid is located in C-terminal direction, i.e., the end of the polypeptide.

A polynucleotide is said to "code for" or to "encode" a polypeptide if, in its native state or when manipulated by methods known in the art, the polynucleotide can be transcribed and/or translated to produce the polypeptide or a fragment thereof.

A "polypeptide binding segment" of a chaperone is considered as that pan of a chaperone that binds and holds the polypeptide chain during the three-dimensional folding process of a protein. The "polypeptide binding segment" of the E. coli chaperone SlyD, i.e., its chaperone properties, have been localized to the so-called IF domain (insert in flap domain, amino acids ~76-122) in this application. As an autonomous folding unit, a protein domain is able to adopt a native-like stable fold in aqueous solution. The terms "polypeptide binding segment", "IF-loop", IF-domain, or chaperone domain may be used synonymously.

Preferred non-human chaperones are E. coli SlyD and SlpA and the FKBP chaperones of archaebacteria such as FKBP17 from Methanococcus thermolithotrophicus, FKBP18 from Methanococcus jannaschii, FKBP18 from Thermococcus sp. KS1, FKBP29 from Pyrococcus horikoshii, FKBP26 from Methanococcus jannaschii, and FKBP30 from Aeropyrum pernix as listed by Suzuki et al. 2003, JMB 328, 1149-1160.

In a preferred embodiment, the at least one nucleotide sequence coding for a polypeptide binding segment of a non-human chaperone protein contains a sequence coding for a non-human FK506 binding protein (FKBP). More preferred are FKBP sequences of E. coli, Methanococcus thermolithotropicus, Methanococcus jannaschii, Thermococcus sp KS1, Pyrococcus horikoshii or Aeropyrum pernix, the E. coli SlyD and SlpA sequences being most preferred.

In a particularly preferred embodiment, the E. coli SlyD sequence contains a nucleotide sequence coding for a polypeptide N-terminally starting with any amino acid located between amino acid no. 56 and 75 of SEQ ID NO: 1 and C-terminally ending with any amino acid located between amino acid no. 122 and 136 of SEQ ID NO: 1. Most preferred is a sequence coding for a polypeptide N-terminally starting with amino acid no. 70 and C-terminally ending with amino acid no. 129 of SEQ ID NO: 1.

In a further preferred embodiment, the E. coli SlpA sequence contains a nucleotide sequence coding for a polypeptide N-terminally starting with any amino acid located between amino acid no. 56 and 75 of SEQ ID NO: 12 and C-terminally ending with any amino acid located between amino acid no. 122 and 136 of SEQ ID NO: 12. Most preferred is a sequence coding for a polypeptide N-terminally starting with amino acid no. 72 and C-terminally ending with amino acid no. 132 of SEQ ID NO: 12.

As to the upstream and downstream sequences adjacent to the nucleotide sequences coding for a polypeptide binding segment of a non-human chaperone protein, these upstream and downstream sequences originate from an FK506 binding protein or an FK506-binding-protein-like domain (also termed FKBP-like domain).

According to the invention, an FK506 binding protein (FKBP) is a protein capable of recognizing and binding the immunosuppressant FK506 with high affinity in the nanomolar range. An FKBP-like domain ("FK506-binding-protein-like domain") or FKBP-like protein is a protein or part of a protein that is no more or barely susceptible to prolyl isomerase inhibition by FK506. These FKBP-like domains share significant sequence and structural similarity with FK506 binding proteins like FKBP12, but some of the amino acid residues mediating FK506 binding are mutated, and the affinity is shifted to the micromolar range. For instance, SlyD and trigger factor, two PPIases from the E. coli cytosol, are envisaged as FKBP-like proteins (Callebaut & Mornon, FEBS Lett. (1995) 374(2) 211-215; Wülfing et al., J. Biol. Chem. (1994) 269(4), 2895-2901)).

With regard to the upstream and downstream sequences adjacent to the nucleotide sequences coding for a polypeptide binding segment of a non-human chaperone protein like *E. coli* SlyD or SlpA, it is preferred that the upstream and/or downstream nucleotide sequence coding for a human peptidyl-prolyl-cis/trans isomerase of the FKBP type contains a nucleotide sequence coding for an FK506 binding protein (FKBP) or a FKBP-like domain, a sequence coding for human FKBP12 being particularly preferred.

Further in a preferred embodiment, the upstream nucleotide sequence coding for FKBP12 contains a sequence coding for a polypeptide N-terminally starting with any amino acid located between amino acid no. 1 to 20 of SEQ ID NO: 3 and C-terminally ending with any amino acid located between amino acid no. 70 to 89 of SEQ ID NO: 3.

Also preferred is an embodiment in which the downstream nucleotide sequence coding for FKBP12 contains a sequence coding for a polypeptide N-terminally starting with any amino acid located between amino acid no. 90 to 97 of SEQ ID NO: 3 and C-terminally ending with any amino acid located between amino acid no. 103 to 107 of SEQ ID NO: 3.

Most preferred is a recombinant DNA molecule that contains a nucleotide sequence coding for a polypeptide according to SEQ ID NO: 4. SEQ ID NO: 4 shows an amino acid sequence that N-terminally starts with amino acid position glycine/G 1 to glycine/G 83 of SEQ ID NO: 3 (FKBP12), continues with amino acid position glutamine/Q 70 to asparagine/N 129 of SEQ ID NO: 1 (SlyD), and ends with leucine/L 97 to glutamic acid/E 107 of SEQ ID NO: 3 (FKBP12). The polypeptide corresponding to the amino acid sequence as shown in SEQ ID NO: 4 is also called FKBP12-IF1.

In a further preferred embodiment of the invention, the recombinant DNA molecule contains a nucleotide sequence coding for a polypeptide according to SEQ ID NO: 13. SEQ ID NO: 13 shows an amino acid sequence that N-terminally starts with amino acid position glycine/G 1 to glycine/G 83 of SEQ ID NO: 3 (FKBP12), continues with amino acid position valine/V72 to threonine/T132 of SEQ ID NO: 12 (SlpA), and ends with leucine/L 97 to glutamic acid/E 107 of SEQ ID NO: 3 (FKBP12). The polypeptide corresponding to the amino acid sequence as shown in SEQ ID NO: 13 is also called FKBP12-IF4.

In a further preferred embodiment of the invention, the recombinant DNA molecule contains a nucleotide sequence coding for a polypeptide according to SEQ ID NO: 15.

SEQ ID NO: 15 shows an amino acid sequence that N-terminally starts with amino acid position glycine/G 1 to glycine/G 83 of SEQ ID NO: 3 (FKBP12), continues with amino acid position methionine/M84 to threonine/T140 of SEQ ID NO: 14 (*Thermococcus* FKBP18), and ends with leucine/L 97 to glutamic acid/E 107 of SEQ ID NO: 3 (FKBP12). The polypeptide corresponding to the amino acid sequence as shown in SEQ ID NO: 15 is also called FKBP12-IF5.

It is advantageous to choose the DNA sequences to be inserted upstream and downstream of the sequence encoding the polypeptide binding segment of a non-human chaperone protein in such a way that the two-dimensional structural elements like β-sheets are not interrupted by heterologous sequence elements but remain intact. The commonly known sequence alignments assist in choosing the suitable upstream and downstream sequences like, for example, Suzuki et al., 2003, JMB 328, 1149-1160.

According to the invention, the choice and arrangement of nucleotide sequences coding for a polypeptide binding segment of a non-human chaperone protein and the upstream and downstream nucleotide sequences, i.e., encoding an FK506 binding protein (FKBP) or an FK506-binding-protein-like domain (FKBP-like domain), and preferably encoding an FKBP type human peptidyl-prolyl-cis/trans isomerase (PPIase), is carried out in such a way that the overall structural order of the resulting chimeric fusion protein corresponds to the structure of a naturally occurring chaperone. In other words, the overall structure preferably maintains the arrangement of secondary structural elements like α-helices and β-sheets as indicated in the state of the art (e.g., Suzuki et al., 2003, JMB 328, 1149-1160).

The invention particularly relates to a chimeric fusion protein produced by expression of such recombinant DNA molecules.

By expression of the above identified recombinant DNA molecules we have been able to provide counterparts to the bacterial PPIase chaperones SlyD, FkpA, trigger factor, and SlpA and even humanized counterparts to the bacterial PPIase chaperones SlyD, trigger factor, and SlpA. These humanized peptidyl-prolyl-cis/trans isomerase chaperones may work as helpful tools in biotechnological applications and as additives in diagnostic tests. As can be seen in the experimental part of this application, we have been able to obtain a humanized chaperone which has a higher catalytic efficiency than the wild type folding helpers, the amino acid sequences of which are contained in the humanized chaperone according to the invention. Based on the observations in an RNase T1 refolding test system which shows the folding and refolding abilities of a protein, we have been able to show that isolated human FKBP12 has only a small catalytic efficiency of about 14,000 $M^{-1}s^{-1}$. The catalytic efficiency of isolated unmodified *E. coli* SlyD reaches 680,000 $M^{-1}s^{-1}$. A deletion variant of SlyD lacking the IF loop domain exhibits a negligible catalytic efficiency of ~500 $M^{-1}s^{-1}$ in the RNase T1 folding assay. Surprisingly, the catalytic efficiency of the chimeric molecule FKBP12-IF1 (amino acid sequence shown in SEQ ID NO: 4) substantially exceeds this value. FKBP12-IF1 shows an outstanding catalytic efficiency of about 2,500,000 $M^{-1}s^{-1}$ (sec also Table 1 in the Examples section), which surpasses the values of the most efficient prolyl isomerases known to date. This value even exceeds the catalytic efficiency of the trigger factor, which amounts to $1.2 \times 10^6 M^{-1}s^{-1}$ (Stoller et al. (1995) *EMBO J.* 14, 4939-4984: Zarnt et al. (1997) *J. Mol. Biol.* 271, 827-837; Scholz et al. (1997) *EMBO J.* 16, 54-58).

By combining the active site of the prolyl isomerase center of a human FK506 binding protein with a polypeptide binding domain, i.e., the so-called IF loop, of a non-human chaperone protein, we have generated a folding helper with superior chaperone and enzymatic properties. We have been able to provide a folding helper with a higher catalytic efficiency than that of the isolated wild type proteins. The folding helper according to the invention may therefore also be called "super chaperone" referring to its superior catalytic efficiency.

Part of the invention therefore is a recombinantly produced fusion protein comprising a) a polypeptide sequence containing the polypeptide binding segment of a non-human chaperone protein, b) a polypeptide sequence of an FK506 binding protein (FKBP) or an FK506-binding-protein-like domain (FKBP-like domain) that is fused to the N-terminal end of the non-human chaperone polypeptide sequence, and c) a polypeptide sequence of an FK506 binding protein (FKBP) or an FK506-binding-protein-like domain (FKBP-like domain) that is fused to the C-terminal end of the non-human chaperone polypeptide sequence.

One of the preferred embodiments therefore is a recombinantly produced fusion comprising a) a polypeptide sequence containing the polypeptide binding segment of a non-human chaperone protein, b) a polypeptide sequence of a human FKBP type peptidyl-prolyl-cis/trans isomerase that is fused to the N-terminal end of the non-human chaperone polypeptide sequence, and c) a polypeptide sequence of a human FKBP type peptidyl-prolyl-cis/trans isomerase that is fused to the C-terminal end of the non-human chaperone polypeptide sequence. A preferred embodiment is a chimeric fusion protein that contains a polypeptide binding segment of an *E. coli* SlyD chaperone sequence and human FKBP12 polypeptide sequences which are N- and C-terminally fused to the SlyD sequence. One of the preferred embodiments of the invention is a chimeric fusion protein containing an amino acid sequence according to SEQ ID NO: 4.

Also preferred is a chimeric fusion protein that contains a polypeptide binding segment of an *E. coli* SlpA chaperone sequence and human FKBP12 polypeptide sequences which are N- and C-terminally fused to the SlpA sequence. More details on a chimeric fusion protein containing a polypeptide binding segment of an E, coli SlpA chaperone sequence are given in the Examples section and in Table 1.

One of the preferred embodiments of the invention is a chimeric fusion protein containing an amino acid sequence according to SEQ ID NO: 13. This protein is called FKPB12-IF4.

Also preferred is a fusion protein that contains a polypeptide binding segment of a *Thermococcus* FKBP18 chaperone sequence and human FKBP12 polypeptide sequences which are N- and C-terminally fused to the *Thermococcus* FKBP18 sequence. *Thermococcus* FKBP18 is a thermostable homologue of SlyD bearing an IF domain in the flap region near the prolyl isomerase active site. The amino acid sequence of *Thermococcus* FKBP18 is shown in SEQ ID NO: 14. The amino acid sequence of the resulting chimeric fusion protein in which the putative IF loop domain of *Thermococcus* FKBP18 is grafted onto the folding scaffold of hFKBP12 is shown in SEQ ED NO: 15. More details on this chimeric fusion protein are given in the Examples section and in Table 1.

In another embodiment of the invention, the IF domain originating from SlyD is inserted into the FKBP domain of the *E. coli* trigger factor. SEQ ID NO: 18 shows the amino acid sequence of this chimeric folding helper protein (trigger factor-IF/SlyD). The IF domain originating from SlyD is inserted into the FKBP domain of the *E. coli* trigger factor. The SlyD insert is underlined.

In a further embodiment, the IF domain originating from SlyD is inserted into the FKBP domain of FkpA (as shown in SEQ ID NO: 20). The resulting chimeric folding helper protein is called FkpA-IF/SlyD. This chimeric folding helper protein is expected to show a high activity in the RNaseT1 folding test. SEQ ID NO: 21 shows the amino acid sequence of the chimeric folding helper protein according to the invention.

From our experiments we infer that the chaperone function of SlyD, SlpA, and TcFKBP18 is confined to the so-called IF (insert in flap) domain. We conclude that the IF domains of different FKBP chaperones are structurally related and functionally equivalent. Thus, IF domains from different FKBP chaperones should be mutually interchangeable. We postulate that the IF domain within SlyD may be replaced by the putative IF domains of, e.g., SlpA or TcFKBP18, without compromising the genuine folding helper properties of SlyD. This interchange of the chaperone domain should be possible in a mutual way, i.e., putative IF domains may be grafted onto the FKBP-like domains of SlpA or TcFKBP18 to yield functional chaperone modules. The interchange of chaperone domains might pave the way for tailor-made folding helpers with a substrate affinity adapted to the respective target protein.

In FKBP-X fusion proteins, FKBP functioning as a carrier module and X meaning guest or target protein, the carrier modules and the guest proteins exist in a dynamic equilibrium between a closed and an open form. In the closed form, hydrophobic regions are shielded, and thus the fusion protein remains soluble and does not aggregate. In the open form, the antigenic sites are exposed, which allows the guest protein to be functional, e.g., in an immunoassay. The affinity must thus be well balanced in the fusion proteins, and it might be adapted to the needs of the target module by interchanging IF-domains from different FKBP chaperones.

Optionally all chimeric fusion proteins may further be fused to a target polypeptide sequence. A target polypeptide according to the present invention may be any polypeptide required in larger amounts and therefore difficult to isolate or purify from other non-recombinant sources.

Examples of target proteins preferably produced by the present methods include mammalian gene products such as enzymes, cytokines, growth factors, hormones, vaccines, antibodies, and the like. More particularly, preferred overexpressed gene products of the present invention include gene products such as erythropoietin, insulin, somatotropin, growth hormone releasing factor, platelet derived growth factor, epidermal growth factor, transforming growth factor α; transforming growth factor, epidermal growth factor, fibroblast growth factor, nerve growth factor, insulin-like growth factor I, insulin-like growth factor II, clotting Factor VIII, superoxide dismutase, interferon, γ-interferon, interleukin-1, interleukin-2, interleukin-3, interleukin-4, interleukin-5, interleukin-6, granulocyte colony stimulating factor, multi-lineage colony stimulating factor, granulocyte-macrophage stimulating factor, macrophage colony stimulating factor, T cell growth factor, lymphotoxin, and the like. Preferred overexpressed gene products are human gene products.

Moreover, the present methods can readily be adapted to enhance secretion of any overexpressed gene product which can be used as a vaccine. Overexpressed gene products which can be used as vaccines include any structural, membrane-associated, membrane-bound, or secreted gene product of a mammalian pathogen. Mammalian pathogens include viruses, bacteria, single-cell, or multi-cell parasites which can infect or attack a mammal. For example, viral vaccines can include vaccines against viruses such as human immunodeficiency virus (HIV), vaccinia, poliovirus, adenovirus, influenza, hepatitis A, hepatitis B, dengue virus, Japanese B encephalitis, Varicella zoster, cytomegalovirus, hepatitis A, rotavirus, as well as vaccines against viral diseases like measles, yellow fever, mumps, rabies, herpes, influenza, parainfluenza, and the like. Bacterial vaccines can include vaccines against bacteria such as *Vibrio cholerae, Salmonella typhi, Bordetella pertussis, Streptococcus pneumoniae, Haemophilus influenzae, Clostridium tetani, Corynebacterium diphtheriae, Mycobacterium leprae, R. rickettsii, Shigella, Neisseria gonorrhoeae, Neisseria meningitidis, Coccidioides immitis, Borrelia burgdorferi*, and the like. Preferably, the target protein is a member of a group consisting of retroviral proteins such as gp41 and p17 from HIV-1, gp36 and p16 from HIV-2, gp21 from HTLV-I/II, consisting of viral envelope proteins such as E1 and E2 from Rubella virus or consisting of amyloidogenic proteins such as β-AP42 (Alzheimer peptide) or prion protein.

A target polypeptide according to the present invention may also comprise sequences, e.g., diagnostically relevant epitopes, from several different proteins constructed to be expressed as a single recombinant polypeptide.

A recombinant DNA molecule encoding a chimeric fusion protein comprising a) at least one nucleotide sequence encoding a polypeptide binding segment of a non-human chaperone protein, b) upstream thereto at least one nucleotide sequence coding for an FK506 binding protein or an FK506-binding-protein-like domain (FKBP-like domain) and c) downstream thereto at least one nucleotide sequence coding for an FK506-binding-protein-like domain (FKBP-like domain) and d) at least one nucleotide sequence encoding a target polypeptide is also an object of the invention.

Preferably, a recombinant DNA molecule encoding a chimeric fusion protein comprising a) at least one nucleotide sequence encoding a polypeptide, binding segment of a non-human chaperone protein, b) upstream thereto at least one nucleotide sequence encoding an FKBP type human peptidyl-prolyl-cis/trans isomerase (PPIase), c) downstream thereto at least one nucleotide sequence encoding an FKBP type human peptidyl-prolyl-cis/trans isomerase (PPIase), and d) at least one nucleotide sequence encoding a target polypeptide is also an object of the invention.

It is important that the nucleotide sequences encoding a target polypeptide are inserted in such a way that the sequence encoding the chimeric super chaperone according to steps a), b), and c) remains intact so that it maintains its catalytic and chaperone functions. This means that the nucleotide sequence encoding the target polypeptide is inserted in frame upstream or downstream of the sequence encoding the chimeric fusion protein. It may also be inserted upstream and downstream and also more than one copy may be inserted.

The recombinant DNA encoding a chimeric fusion protein and a target polypeptide according to the invention may also comprise a linker sequence resulting in a linker polypeptide after expression of the complete protein. As the skilled artisan will appreciate, such linker polypeptide is designed as most appropriate for the intended application, especially in terms of length, flexibility, charge, and solubility.

Variants of the chimeric fusion proteins bearing one or several amino acid substitutions or deletions may also be used to obtain a recombinant DNA or a chimeric fusion protein according to the invention. Somebody skilled in the art may easily assert whether such variants are appropriate for a method of the invention by using the procedures as described in the Examples section.

Large amounts of the polynucleotides may be produced by replication in a suitable host cell. Natural or synthetic DNA fragments coding for proteins or fragments thereof will be incorporated into recombinant polynucleotide constructs, typically DNA constructs, capable of introduction into and replication in a prokaryotic or eukaryotic cell.

The polynucleotides may also be produced by chemical synthesis including, hut not limited to, the phosphoramidite method described by Beaucage, S. L., and Caruthers, M. H., Tetrahedron Letters 22 (1981) 1859-1862, and the triester method according to Matteucci. M. D. and Caruthers. M. H. J. Am. Chem. Soc. 103 (19881) 3185-3191. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide sequences are operably linked when they are placed into a functional relationship with another polynucleotide sequence. For instance, a promoter is operably linked to a coding sequence if the promoter affects transcription or expression of the coding sequence. Generally, "operably linked" means that the linked sequences are contiguous and, where necessary to join two protein coding regions, both contiguous and in reading frame. However, it is well known that certain genetic elements, such as enhancers, may be operably linked even at a distance, i.e., even if not contiguous.

DNA constructs prepared for introduction into a host typically comprise a replication system recognized by the host, including the intended DNA fragment encoding the desired chimeric fusion peptide and optionally an additional target polypeptide and will preferably also include transcription and translational initiation regulatory sequences operably linked to the polypeptide encoding segment. Expression systems (expression vectors) may include, for example, an origin of replication or autonomously replicating sequence (ARS) and expression control sequences, a promoter, an enhancer, and necessary processing information sites such as ribosome-binding sites, RNA splice sites, polyadenylation sites, transcriptional terminator sequences, and mRNA stabilizing sequences.

The appropriate promoter and other necessary vector sequences are selected so as to be functional in the host. Examples of workable combinations of cell lines and expression vectors include but are not limited to those described Sambrook, J., et al. in "Molecular Cloning: A Laboratory Manual" (1989), Eds. J. Sambrook, E. F. Fritsch and T. Maniatis, Cold Spring Harbour Laboratory Press, Cold Spring Harbour or Ausubel, F., et al., in "Current protocols in molecular biology" (1987 and periodic updates), Eds. F. Ausubel, R. Brent and K. R. E., Wiley & Sons Verlag, New York; and Metzger, D., et al., Nature 334 (1988) 31-6. Many useful vectors for expression in bacteria, yeast, mammalian, insect, plant, or other cells are known in the art and may be obtained from vendors including but not limited to Stratagene, New England Biolabs, Promega Biotech, and others. In addition, the construct may be joined to an amplifiable gene (e.g., DHFE) so that multiple copies of the gene may be obtained.

Expression and cloning vectors will likely contain a selectable marker, a gene encoding a protein necessary for the survival or growth of a host cell transformed with the vector, although such a marker gene may be carried on another polynucleotide sequence co-introduced into the host cell. Only those host cells expressing the marker gene will survive and/or grow under selective conditions. Typical selection genes include but are not limited to those encoding proteins that (a) confer resistance to antibiotics or other toxic substances, e.g., ampicillin, tetracycline, etc., (b) complement auxotrophic deficiencies, or (c) supply critical nutrients not available from complex media. The choice of the proper selectable marker will depend on the host cell, and appropriate markers for different hosts are known in the art.

According to the invention, an expression vector comprising operably linked a recombinant DNA molecule according to the present invention, i.e., comprising a) at least one nucleotide sequence coding for a polypeptide binding segment of a non-human chaperone protein, b) upstream thereto at least one nucleotide sequence coding for an FK506 binding protein or an FK506-binding-protein-like domain (FKBP-like domain), c) downstream thereto at least one nucleotide sequence coding for an FK506-binding-protein-like domain (FKBP-like domain), and optionally d) at least one nucleotide sequence encoding a target polypeptide, has proven to be very advantageous.

An expression vector comprising operably linked a recombinant DNA molecule according to the present invention, i.e., comprising a) at least one nucleotide sequence coding for a polypeptide binding segment of a non-human chaperone protein, b) upstream thereto at least one nucleotide sequence coding for a human peptidyl-prolyl-cis/trans isomerase (PPIase) of the FKBP type, c) downstream thereto at least one nucleotide sequence coding for a human peptidyl-prolyl-cis/ trans isomerase (PPIase) of the FKBP type, and optionally d) at least one nucleotide sequence encoding a target polypeptide, is also part of the invention.

The vectors containing the polynucleotides of interest can be introduced into the host cell by any method known in the art. These methods vary depending upon the type of cellular host, including but not limited to transfection employing calcium chloride, rubidium chloride, calcium phosphate, DEAE-dextran, other substances, and infection by viruses. Large quantities of the polynucleotides and polypeptides of the present invention may be prepared by expressing the polynucleotides of the present: invention in vectors or other expression vehicles in compatible host cells. The most commonly used prokaryotic hosts are strains of *Escherichia coli*, although other prokaryotes, such as *Bacillus subtilis* may also be used. Expression in *Escherichia coli* represents a preferred mode of carrying out the present invention.

Construction of a vector according to the present invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridization, using an appropriately labeled probe which may be based on a sequence provided herein. Those skilled in the art will readily envisage how these methods may be modified, if desired.

The expression vector comprising a recombinant DNA according to the present invention may be used to express the fusion protein in a cell free translation system or may be used to transform a host cell. In a preferred embodiment the present invention relates to a host cell transformed with an expression vector according to the present invention.

In a further preferred embodiment the present invention relates to a method of producing a chimeric fusion protein. Said method comprising the steps of culturing a host cell transformed with an expression vector according to the present invention, expression of that chimeric fusion protein in the respective host cell and purification of said chimeric fusion protein.

The chimeric fusion proteins according to the invention show a high solubility. When overexpressed in the cytosol they mainly accumulate in the soluble fraction. To a smaller extent they are also expressed in inclusion bodies. Generally cells are lysed under appropriate buffer conditions like e.g., in chaotropic substances. When the chimeric fusion proteins are tagged with a hexa-histidine (SEQ ID NO: 24) moiety unfolded proteins may be bound to a nickel-containing column (Ni-NTA) where they are also refolded under appropriate buffer conditions. Such purification and refolding protocols as shown in more detail in the Examples section are well known to the skilled artisan.

Due to their superior folding helper properties, the chimeric fusion proteins according to the invention may be applied as folding helpers for any target protein which otherwise would not adopt its proper three-dimensional structure, i.e., its native-like conformation. According to the invention the chimeric fusion proteins may also be used as folding helpers in the process of production of target proteins. For example, after primary solubilization of the overproducing host cell, an overexpressed target protein usually does not yet adopt its native structure due to chaotropic substances or due to the presence of detergents or other buffer conditions which compromise the native conformational state of a target protein. The chimeric fusion proteins may then be added during the process of purification and solubilization of the target protein and may help in the process of refolding and renaturation.

As for an application in coupled transcription/translation systems, cell lysates containing the overexpressed chimeric folding helper may be added to the vial in which the in vitro translation is carried out so that the proper conformational folding of the translated protein is facilitated.

The chimeric fusion proteins according to the invention may be applied in an immunoassay to help in the process of immunological binding of antigens and antibodies to their binding partners without disturbing the immunoassay and its results. It is advantageous that the chimeric fusion proteins according to the invention are humanized, i.e., they contain mainly human amino acid sequences so that the probability of interferences due to naturally occurring antibodies in human samples against non-human protein sequences is minimized. Preferably the percentage of amino acids originating from human sequences is at least 60% compared to the complete amino acid sequence of the chimeric fusion protein.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates in "Practice and theory of enzyme immunoassays" (1990) 221-278, Eds. R. H. Burdon and v. P. H. Knippenberg. Elsevier. Amsterdam) and various volumes of Tijssen, in "Methods in Enzymology" (1980), Eds. S. P. Colowick, N. O. Caplan and S. P., Academic Press), dealing with immunological detection methods, especially volumes 70, 73, 74, 84, 92 and 121.

In further embodiments of the invention the chimeric fusion proteins may be used as a fusion partner in the process of production of target proteins, in the production of a vaccine or in the process of producing pharmaceuticals, respectively.

In case a therapeutic application of the novel chimeric fusion proteins is intended, preferably a composition comprising a recombinantly produced chimeric fusion protein according to the present invention and a pharmaceutically acceptable excipient will be formulated.

The examples and figures are provided to aid the understanding of the present invention, the true scope of which is set forth in the appended claims, it is understood that modifications can be made in the procedures set forth without departing from the spirit of the invention.

EXAMPLES

Materials and Reagents

Guanidinium chloride (GdmCl, A-grade) was purchased from NIGU (Waldkraiburg, Germany). Complete EDTA-free protease inhibitor tablets, imidazole, and EDTA were from Roche Diagnostics GmbH (Mannheim, Germany). All other chemicals were analytical grade from Merck (Darmstadt, Germany). (S54G, P55N)-RNase T1 was purified, reduced, and carboxymethylated as described by Mücke, M., and Schmid, F. X. (1994.) J. Mol. Biol. 239, 713-725. Ultrafiltration membranes (YM10, YM30) were purchased from Amicon (Danvers, Mass., USA), microdialysis membranes (VS/0.025 μm) and ultrafiltration units (biomax ultrafree filter devices) were from Millipore (Bedford, Mass., USA). Cellulose nitrate and cellulose acetate membranes (1.2 μm/0.45 μm/0.2 μm) for the filtration of crude lysates were from Sartorius (Göittingen, Germany).

Example 1

Production of a Chimeric Fusion Protein hFKBP12-IF1 Containing *E. coli* SlyD and Human FKBP12 Sequences Cloning of Expression Cassettes The sequences of hFKBP12 and SlyD were retrieved from the SwissProt database. Synthetic genes encoding hFKBP12 and its insertion variants were purchased from Medigenomix (Martinsried, Germany) and cloned into pET24 expression vectors (Novagen, Madison, Wis., USA). The codon usage was optimized for expression in *E. coli* host cells. The gene for SlyD was amplified by PCR from *E. coli* strain BL21 (DE3), restricted and ligated into the pET24a expression vector. The expression cassettes for the fusion proteins were designed as described for the *E. coli* SlyD* fusion module as described by Scholz et al. (2005) in J. Mol. Biol. 345, 1229-1241.

A synthetic gene (residues 1-155 of SEQ ID NO: 10) encoding the protein FKBP12-IF1 (also shown in SEQ ID NO: 10 with hexa-histidine tag (SEQ ID NO: 24))

```
MGVQVETISP GDGRTFPKRG QTCVVHYTGM LEDGKKFDSS

RDRNKPFKFM LGKQEVIRGW EEGVAQMSVG QRAKLTISPD

YAYGQYDENL VQRVPKDVFM GVDELQVGMR FLAETDQGPV

PVEITAVEDD HVVVDGNHML AGQNLVFDVE LLKLE
``` was purchased from Medigenomix (Martinsried, Germany) and cloned into the pET24a expression vector (Novagen, Madison, Wis.). The codon usage was optimized for expression in *E. coli* host cells. QUIKCHANGE (Stratagene, La Jolla. CA) was used to generate the cysteine-free variant (C22A). The N-terminal methionine is cleaved off after translation by the bacterial N-methionyl-aminopeptidase, so the mature polypeptide actually starts with glycine 1.

```
To obtain thc FKBP12-IF1(C22A)-gp4 fusion
construct (SEQ ID NO:11),
MGVQVETISP GDGRTFPKRG QTAVVHYTGM LEDGKKFDSS

RDRNKPFKFM LGKQEVIRGW EEGVAQMSVG QRAKLTISPD

YAYGQYDENL VQRVPKDVFM GVDELQVGMR FLAETDQGPV

PVEITAVEDD HVVVDGNHML AGQNLVFDVE LLKLEGGGSG

GGSGGGSGGG SGGGSGGGTL TVQARQLLSG IVQQQNNELR

AIEAQQHLEQ LTVWGTKQLQ ARELAVERYL KDQQLLGIWG

CSGKLICTTA VPWNASWSNK SLEQIWNNMT WMEWDREINN

YTSLIHSLIE ESQNQQEKNE QELLELDKWA SLWNWFNITN

WLWYLEHHHH HH
```

DNA fragments encoding NdeI/BamHI-flanked FKBP12-IF1-$(GGGS)_2$GG (SEQ ID NO: 25) and BamHI/XhoI-flanked $(GGGS)_2$GG-gp41 (residues 536 to 681) (SEQ ID NO: 25) were amplified by PCR and inserted in pET24a using NdeI and XhoI. The synthetic gene encoding FKBP12-IF1 (C22A) or purified RNA of a HIV-1 isolate served as PCR-(RT-PCR)-templates. Point mutations L555E, L566E, I573T and I580E were introduced into the gp41 cassette using QUIKCHANGE.

```
The tandem FKBP12-IF1(C22A)-FKBP12-IF1(C22A)-gp41
fusion construct (SEQ ID NO.7)
MGVQVETISP GDGRTFPKRG QTAVVHYTGM LEDGKKFDSS

RDRNKPFKFM LGKQEVIRGW EEGVAQMSVG QRAKLTISPD

YAYGQYDENL VQRVPKDVFM GVDELQVGMR FLAETDQGPV

PVEITAVEDD HVVVDGNHML ACQNLVFDVE LLKLEGGGSG

GGSGGGSGGG SGGGSGGGGV QVETISPGDG RTFPKRGQTA

VVHYTGMLED GKKFDSSRDR NKPFKFMLGK QEVIRGWEEG

VAQMSVGQRA KLTISPDYAY GQYDENLVQR VPKDVFMGVD

ELQVGMRFLA ETDQGPVPVE ITAVEDDHVV VDGNHMLAGQ

NLVFDVELLK LEGGGSGGGS GGGSGGGSGG GSGGGTLTVQ

ARQLLSGIVQ QQNNELRAIE AQQHLEQLTV WGTKQLQARE
LAVERYLKDQ QLLGIWGCSG KLICTTAVPW NASWSNKSLE
QIWNNMTWME WDREINNYTS LIHSLIEESQ NQQEKNEQEL
LELDKWASLW NWFNITNWLW YLEHHHHHH
``` was generated by cleaving FKBP12-IF1(C22A)-gp41 with BamHI and inserting a DNA fragment encoding BamHI/BamHI-flanked $(GGGS)_2$GGG-F12IF1-$(GGGS)_2$GG (The "GGGS)$_2$GGG" linker is disclosed as SEQ ID NO: 27 and the "$(GGGS)_2$GG" linker is disclosed as SEQ ID NO: 25) which was PCR-amplified from the synthetic gene encoding FKBP12-IF1(C22A).

EcSlyD-$[GGGS]_5$GGG-EcSlyD-$[GGGS]_5$GGG-gp41 (536-681; L555E, L566E, I573T, I580E)-HGHDHDHD-His6, pET24a (The "$[GGGS]_5$GGG" linker is disclosed as SEQ ID NO: 22 and the "HG$[HD]_4$His6" spacer is disclosed as SEQ ID NO: 27.)

```
MKVAKDLVVS LAYQVRTEDG VLVDESPVSA PLDYLHGHGS
LIEGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDRHH
DHDHDGGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN
VEVVAIREAT EEELAHGHVH GAHDHHHDHD HDGGGSGGGS
GGGSGGGSGG GSGGGTLTVQ ARQLLSGIVQ QQNNELRAIE
AQQHLEQLTV WGTKQLQARE LAVERYLKDQ QLLGIWGCSG
KLICTTAVPW NASWSNKSLE QIWNNMTWME WDREINNYTS
```

-continued

LIHSLIEESQ NQQEKNEQEL LELDKWASLW NWFNITNWLW

YHGHDHDHDH HHHHH

QUIKCHANGE (Stratagene, La Jolla, USA) and standard PCR techniques were used to generate point mutations, deletion and insertion variants or restriction sites. All recombinant hFKBP12 variants contained a C-terminal hexahistidine tag (SEQ ID NO: 24) to facilitate Ni-NTA-assisted purification and refolding.

Expression, Purification and Refolding of hFKBP12 Variants

All hFKBP12, SlyD and SlpA variants as well as the fusion proteins were purified by using virtually identical protocols. E. coli BL21 (DE3) cells harboring the particular pET24a expression plasmid were grown at 37° C. in LB medium plus kanamycin (30 µg/ml) to an $OD_{600}$ of 1.5, and cytosolic over-expression was induced by adding 1 mM isopropyl-β-D-thiogalactoside. Three hours after induction, cells were harvested by centrifugation (20 min at 5000 g), frozen and stored at −20° C. For cell lysis, the frozen pellet was resuspended in chilled 50 mM sodium phosphate pH 8.0, 7.0 M GdmCl, 5 mM imidazole and the suspension was stirred for 2 h on ice to complete cell lysis. After centrifugation and filtration (cellulose nitrate membrane, 0.45 µm/0.2 µm), the lysate was applied onto a Ni-NTA column equilibrated with the lysis buffer including 5.0 mM TCEP. The subsequent washing step was tailored for the respective target protein and ranged from 5-15 mM imidazole in 50 mM sodium phosphate pH 8.0, 7.0 M GdmCl, 5.0 mM TCEP. At least 10-15 volumes of the washing buffer were applied. Then, the GdmCl solution was replaced by 50 mM sodium phosphate pH 7.8, 100 mM NaCl, 10 mM imidazole, 5.0 mM TCEP to induce conformational refolding of the matrix-bound protein. In order to avoid reactivation of copurifying proteases, a protease inhibitor cocktail (Complete EDTA-free, Roche) was included in the refolding buffer. A total of 15-20 column volumes of refolding buffer were applied in an overnight reaction. Then, both TCEP and the Complete EDTA-free inhibitor cocktail were removed by washing with 3-5 column volumes 50 mM sodium phosphate pH 7.8, 100 mM NaCl, 10 mM imidazole. The native protein was then eluted by 250 mM imidazole in the same buffer. Protein-containing fractions were assessed for purity by Tricine-SDS-PAGE and pooled. Finally, the proteins were subjected to size-exclusion-chromatography (Superdex HiLoad, Amersham Pharmacia) and the protein-containing fractions were pooled and concentrated in an Amicon cell (YM10).

Figure 1:
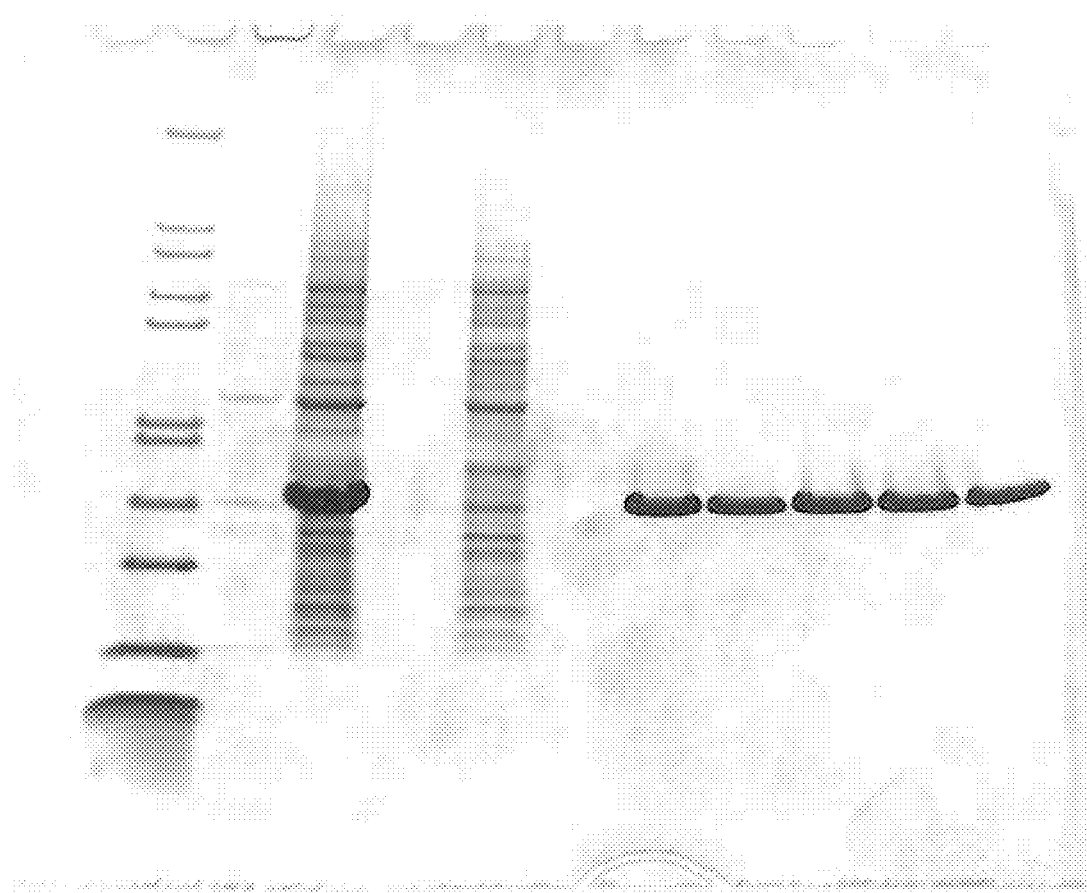
FIG. 1: Purification of FKBP12-IF1 (with SlyD insert) as documented by SDS-PAGE. Lane 1, protein standard Mark 12 Unstained from Invitrogen; lane 3, chaotropic crude lysate of the overproducing E. coli strain BL21/DE 3; lane 5, IMAC flowthrough; lanes 7 to 11, imidazole elution fractions. FKBP12-IF1 can be purified and refolded with high yields in a simple one-step protocol described in the Examples section.

After the coupled purification and refolding protocol, more than 20 mg of target protein could be obtained from 1 g of E. coli wet cells. We further increased the overall solubility of the various hFKBP12 variants by changing cysteine 22 to alanine. The substitution of this single cysteine abolished the tendency of hFKBP12 to form covalent disulfide adducts. It did not affect either the fold of the protein nor its prolyl isomerase activity. The substitution of cysteine 22 for an alanine also turned out to be advantageous in the case of the chimeric protein FKBP12-IF1. The purification of hFKBP12-IF1 (C22A) as documented by SDS-PAGE is shown in FIG. 1.

Example 2

Spectroscopic Measurements

Protein concentration measurements were performed with an Uvikon XL double-beam spectrophotometer. The molar extinction coefficients ($\lambda_{280}$) were determined by using the procedure described by Pace (1995), Protein Sci. A, 2411-2423.

Near-UV CD spectra were recorded with a Jasco-720 spectropolarimeter with a thermostatted cell holder and convened to mean residue ellipticity. The buffer was 50 mM sodium phosphate pH 7.5, 100 mM NaCl, 1 mM EDTA. The path length was 0.5 cm or 1.0 cm, the protein concentration was 20-500 µM. The band width was 1 nm, the scanning speed was 20 nm/min at a resolution of 0.5 nm and the response was 2 s. In order to improve the signal-to-noise ratio, spectra were measured nine times and averaged.

Assessment of Native-Like Fold by Near-UV CD

Figure 2:
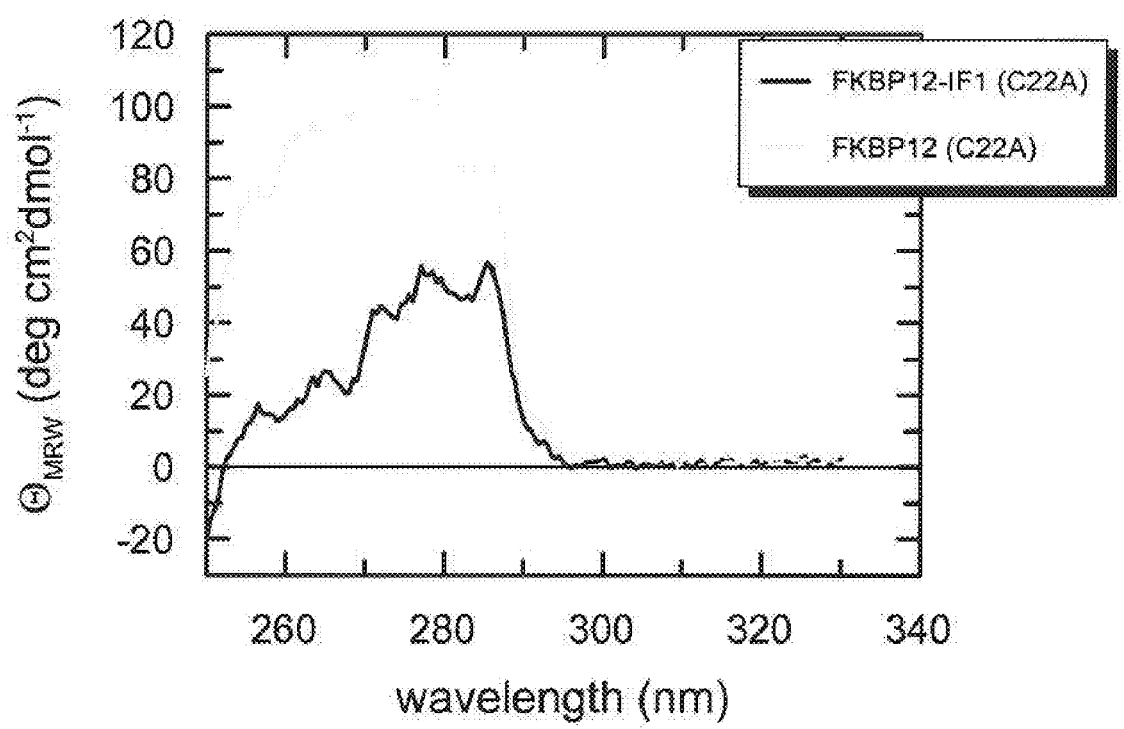
FIG. 2: Near-UV CD spectra of wild type hFKBP12 (gray line) and hFKBP12-IF1 (black line) according to the invention. The buffer was 50 mM sodium phosphate pH 7.5, 100 mM NaCl, 1 mM EDTA, the protein concentration was 100 µM. CD signals between 250 and 310 nm report on the asymmetric environment of the aromatic amino acid residues. The mean residue weight ellipticity of hFKBP12 decreases upon insertion of the SlyD IF loop. Nevertheless, the diminished ellipticity still points to a compact, native-like conformation of the FKBP12-IF1 chimera (black line).

To examine whether the chimeric fusion proteins according to the invention adopt a folded conformation after the coupled purification and refolding protocol, we measured CD spectra in the near-UV region. Near UV-CD reports on the asymmetric environment of aromatic residues in a protein and is therefore a sensitive test for ordered tertiary structure. Grafting a domain such as the SlyD IF loop into the hFKBP12 flap segment might seriously compromise the overall structure of the hFKBP12 scaffold protein. Native human FKBP12 has a typical CD signature in the near-UV region (FIG. 2). Thus, structural distortions or clashes due to the IF-loop-insertion should be visible in the near-UV CD spectrum. FIG. 2 shows an overlay of the spectra of hFKBP12 and hFKBP12-IF1, respectively. Surprisingly, the insertion of the IF domain in the flap region of hFKBP12 leaves the overall structure of the scaffold protein essentially intact. The signature of the spectra is similar, even though the converted ellipticity virtually significantly decreases with the loop insert. Since global unfolding would abolish any near-UV CD signal, this result is strongly indicative that a native-like fold of the chimeric construct hFKBP12-IF1 is essentially retained.

Figure 3:
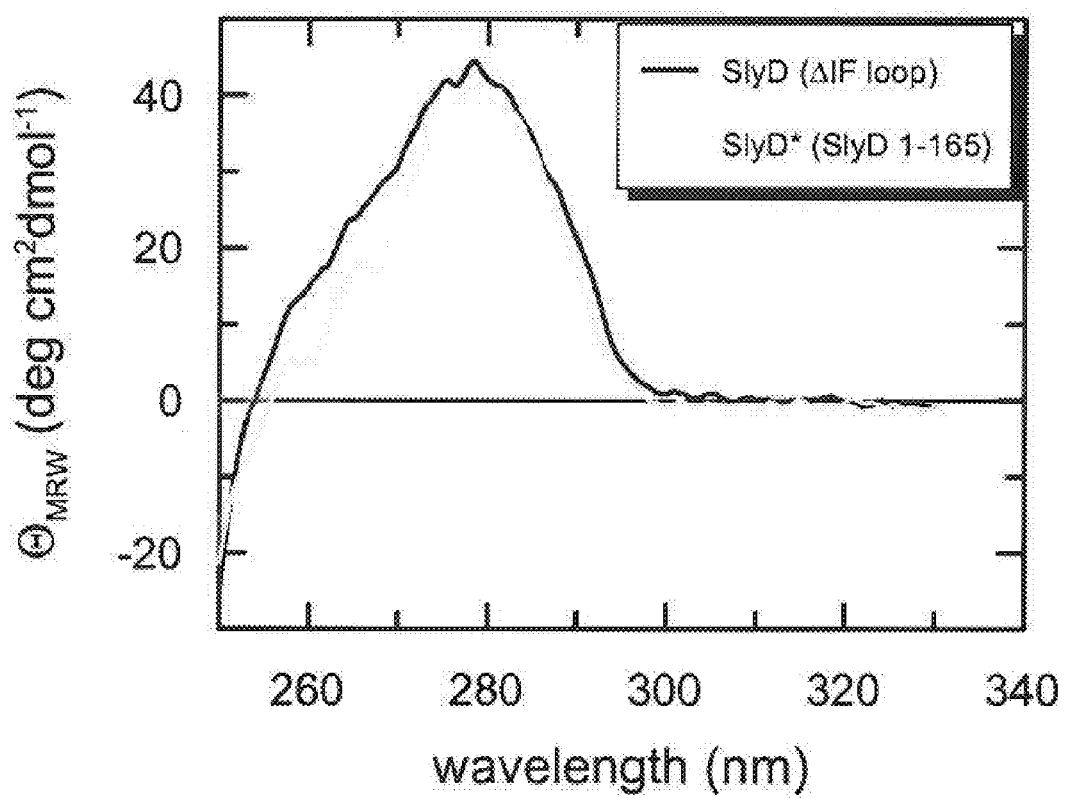
FIG. 3: Near-UV CD spectra of SlyD (1-165, SlyD*) with and without the insert in flap domain. The buffer was 50 mM sodium phosphate pH 7.5, 100 mM NaCl, 1 mM EDTA, the protein concentration was 200 µM SlyD* and 250 µM SlyD* (Δ IF loop). The four tyrosine residues of SlyD* cause a mean residue weight ellipticity of ~40 deg cm$^2$ dmol$^{-1}$ at 278 nm (gray line). When the insert in flap domain is removed, the shape of the near-UV CD signal is essentially retained, but its intensity increases (black line). This highlights that the structural integrity of SlyD* is largely retained after deletion of the IF loop domain. In other words, it stresses the domain character of the IF loop.

Similarly, we recorded near-UV CD spectra for SlyD* (SlyD 1-165) and its deletion variant SlyD* ΔIF-loop (SlyD* lacking amino acid residues 70-129). The results are shown in FIG. 3. As judged by the near-UV CD spectra, the overall structure of SlyD* remains intact when the large "insert in flap" (IF) domain is removed. The mean residue converted ellipticity even slightly increases upon removal of the IF loop. Thus, there is compelling evidence that SlyD lacking its IF domain is still a native-like folded protein.

Example 3

Folding Experiments

For folding studies reduced and carboxymethylated RNase T1 (RCM-T1) was used. RCM-T1 was unfolded by incubating the protein in 0.1 M Tris-HCl pH 8.0 at 15° C. for at least 1 h. Refolding at 15° C. was initiated by a 40-fold dilution of the unfolded protein to final conditions of 2.0 M NaCl and the desired concentrations of SlyD, the FKBP12 variants and RCM-T1 in the same buffer. The folding reaction was followed by the increase in protein fluorescence (i.e., tryptophan fluorescence) at 320 nm (10 nm band width) after excitation at 268 nm (1.5 nm band width). At 2.0 M NaCl slow folding of RCM-T1 was a monoexponential process, and its rate constant was determined by using the program GraFit 3.0 (Erithacus Software, Staines, UK).

Folding Activity of Chimeric Fusion Proteins

We investigated the efficiencies of chimeric fusion proteins according to the invention in the catalysis of a proline-limited protein folding reaction. Reduced and carboxymethylated RNaseT1 (RCM-T1) was used as the model substrate. Its refolding reaction is accompanied by a strong increase in tryptophan fluorescence and can be induced by increasing the NaCl concentration as described by Schmid, F. X. (1991) *Curr. Opin. Struct. Biol.* 1, 36-41, Mayr et al. (1996) *Biochemistry* 35, 5550-5561 and Mücke, M., and Schmid, F. X. (1994) *Biochemistry* 33, 14608-14619.

Figure 4:
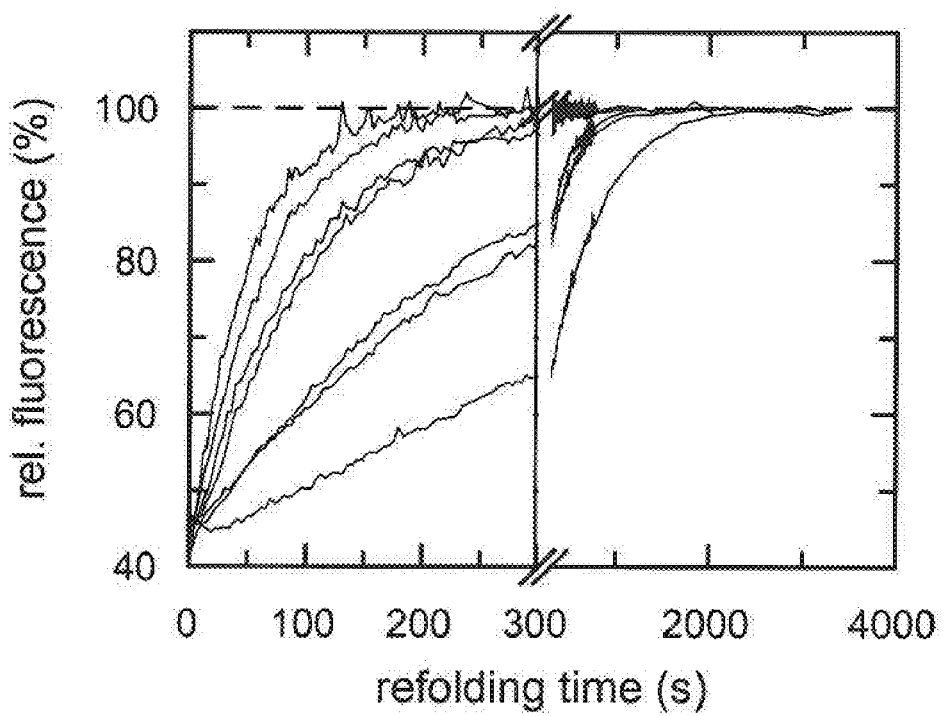
FIG. 4: Refolding kinetics of RCM-T1 in the presence of increasing concentrations of E. coli SlyD* (1-165) at 15° C. (A) The kinetics of refolding of 100 nM RCM-T1, as followed by the change in fluorescence at 320 nm, are shown in the presence of 0, 3, 5, 8, 10, 15 and 20 nM E. coli SlyD*. (B) Dependence on SlyD* concentration of the rate of slow folding. The ratio of the observed rate constants in the presence, $k_{app}$, and in the absence, $k_0$, of SlyD* is shown as a function of the SlyD* concentration. A value of $0.68\times10^6$ M$^{-1}$s$^{-1}$ is obtained for $k_{cat}/K_M$ from the slope of the line in (B). Refolding of RCM-T1 in 0.1 M Tris-HCl, pH 8.0 was initiated by dilution to 2.0 M NaCl in the same buffer.
Figure 4:
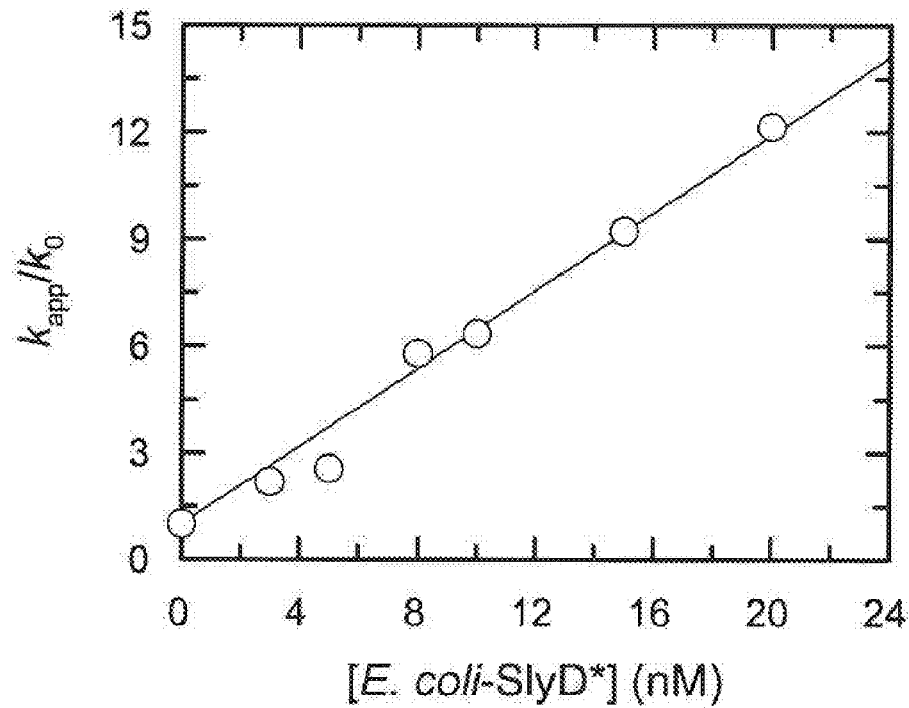

SlyD* (1-165) from *E. coli* catalyzes the refolding of RCM-T1 very well. In the presence of as low as 2 nM SlyD* refolding of RCM-T1 is already twofold accelerated (FIG. 4A). The apparent first-order rate constant of folding $k_{app}$ increases linearly with SlyD* concentration (FIG. 4B). From the slope of this plot, a specificity constant $k_{cat}/K_M$ of $0.68 \times 10^6$ $M^{-1}s^{-1}$ was determined. This is an extraordinarily high value, which almost reaches the catalytic efficiency of trigger factor, the most efficient folding helper known to date (see Stoller et al (1995) *EMBO J.* 14, 4939-4948, Scholz et al. (1997) *EMBO J.* 16, 54-58 and Scholz et al. (1998) *J. Mol. Biol.* 277, 723-732).

Figure 5:
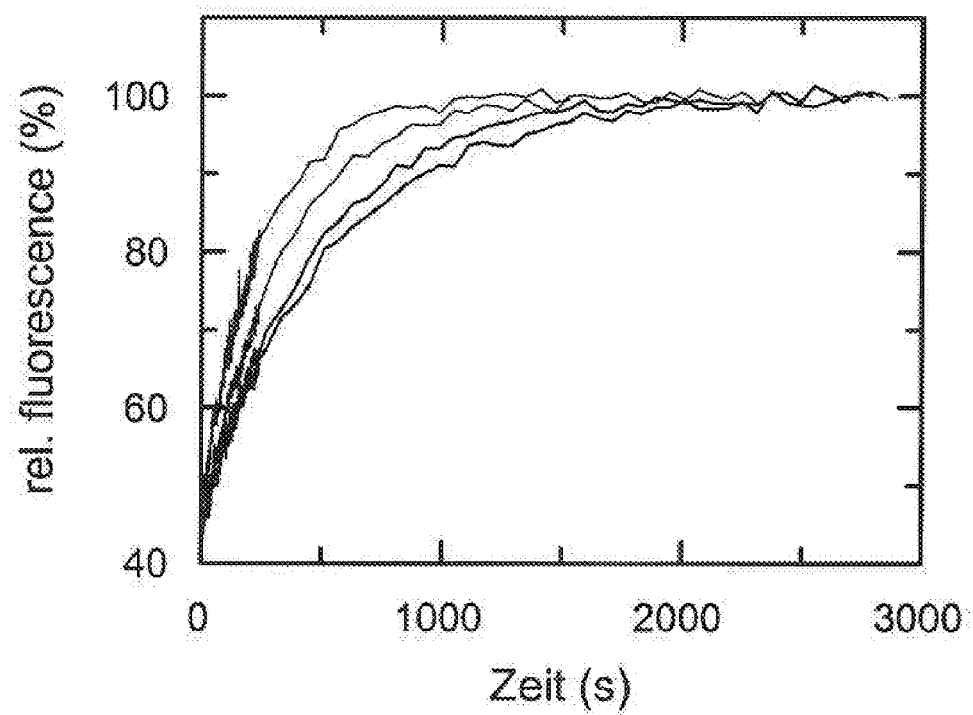
FIG. 5: Refolding kinetics of RCM-T1 in the presence of increasing concentrations of the SlyD deletion variant SlyD (Δ IF loop) at 15° C. (A) The kinetics of refolding of 100 nM RCM-T1, as followed by the change in fluorescence at 320 nm, are shown in the presence of 0, 1.0, 2.0 and 5.0 µM SlyD (Δ IF loop). (B) Dependence on SlyD (Δ IF loop) concentration of the rate of slow folding. The ratio of the observed rate constants in the presence, $k_{app}$, and in the absence, $k_0$, of SlyD (Δ IF loop) is shown as a function of the SlyD (Δ IF loop) concentration. A value of ~500 M$^{-1}$s$^{-1}$ is obtained from the slope of the line in (B). Refolding of RCM-T1 in 0.1 M Tris-HCl, pH 8.0 was initiated by dilution to 2.0 M NaCl in the same buffer.
Figure 5:
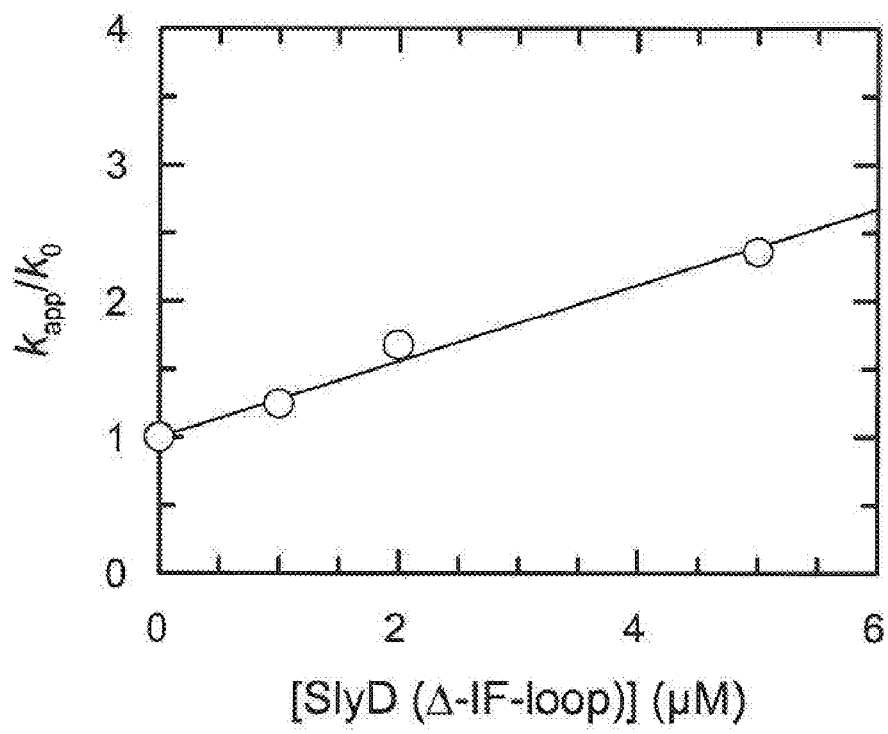

In contrast, the SlyD mutant lacking the IF domain is a very poor catalyst of RCM-T1 refolding. SlyD Δ IF represents the FKBP-domain of SlyD. Its specificity constant ranges around $0.0005 \times 10^6$ $M^{-1}s^{-1}$ and thus amounts to only 0.07% of SlyD* (FIG. 5A/B). This strongly indicates a crucial role of the "insert in flap" domain for binding of unfolded protein substrates. Since the near-UV CD spectra point to a native-like overall fold of the deletion variant (FIG. 3), the insert in flap domain probably represents the polypeptide-binding domain, i.e., the chaperone domain of SlyD.

Figure 6:
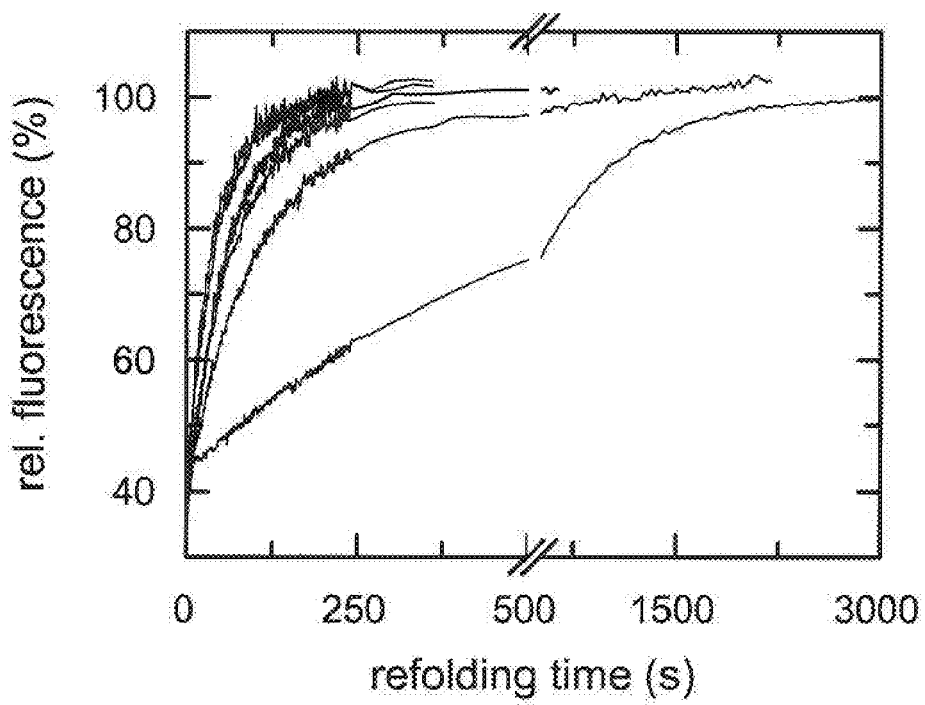
FIG. 6: Refolding kinetics of RCM-T1 in the presence of increasing concentrations of the human prolyl isomerase FKBP12 at 15° C. (A) The kinetics of refolding of 100 nM RCM-T1, as followed by the change in fluorescence at 320 nm, are shown in the presence of 0, 0.5, 0.8, 1.0, 1.5 and 2.0 µM hFKBP12. (B) Dependence on hFKBP12 concentration of the rate of slow folding. The ratio of the observed rate constants in the presence, $k_{app}$, and in the absence, $k_0$, of hFKBP12 is shown as a function of the hFKBP12 concentration. A value of $0.014\times10^6$ M$^{-1}$s$^{-1}$ is obtained for $k_{cat}/K_M$ from the slope of the line in (B). Refolding of RCM-T1 in 0.1 M Tris-HCl, pH 8.0 was initialed by dilution to 2.0 M NaCl in the same buffer.
Figure 6:
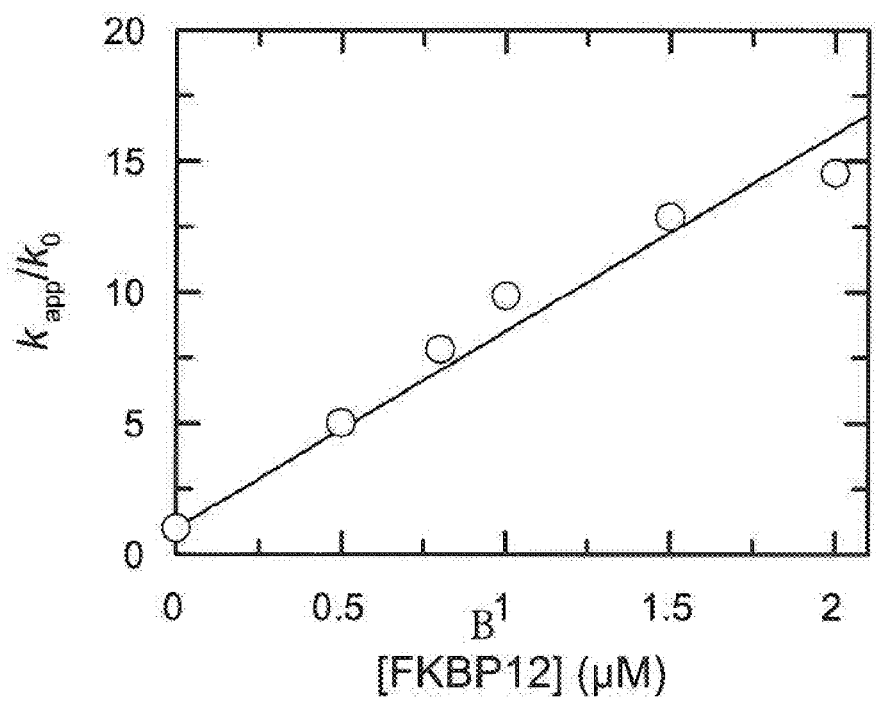
Figure 7:
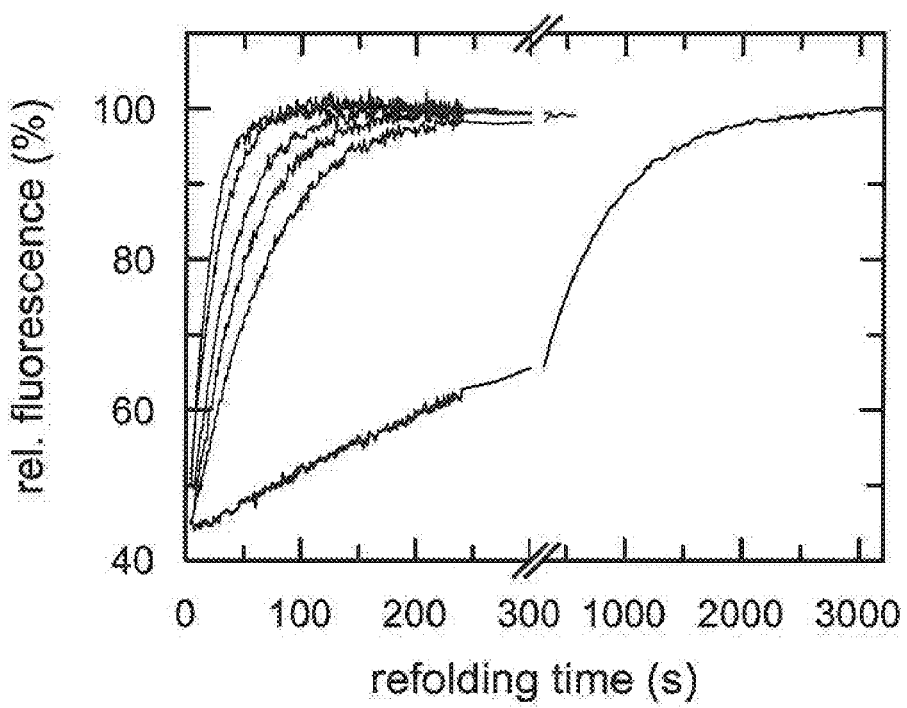
FIG. 7: Refolding kinetics of RCM-T1 in the presence of increasing concentrations of the chimeric protein hFKBP12-IF1 according to the invention at 15° C. (A) The kinetics of refolding of 100 nM RCM-T1, as followed by the change in fluorescence at 320 nm, are shown in the presence of 0, 3, 5, 8, 10 and 20 nM hFKBP12-IF1. (B) Dependence on hFKBP12-IF1 concentration of the rate of slow folding. The ratio of the observed rate constants in the presence, $k_{app}$, and in the absence, $k_0$, of hFKBP12-IF1 is shown as a function of the hFKBP12-IF1 concentration. A value of $2.5\times10^6$ M$^{-1}$s$^{-1}$ is obtained for $k_{cat}/K_M$ from the slope of the line in (B). Refolding of RCM-T1 in 0.1 M Tris-HCl, pII 8.0 was initiated by dilution to 2.0 M NaCl in the same buffer.
Figure 7:
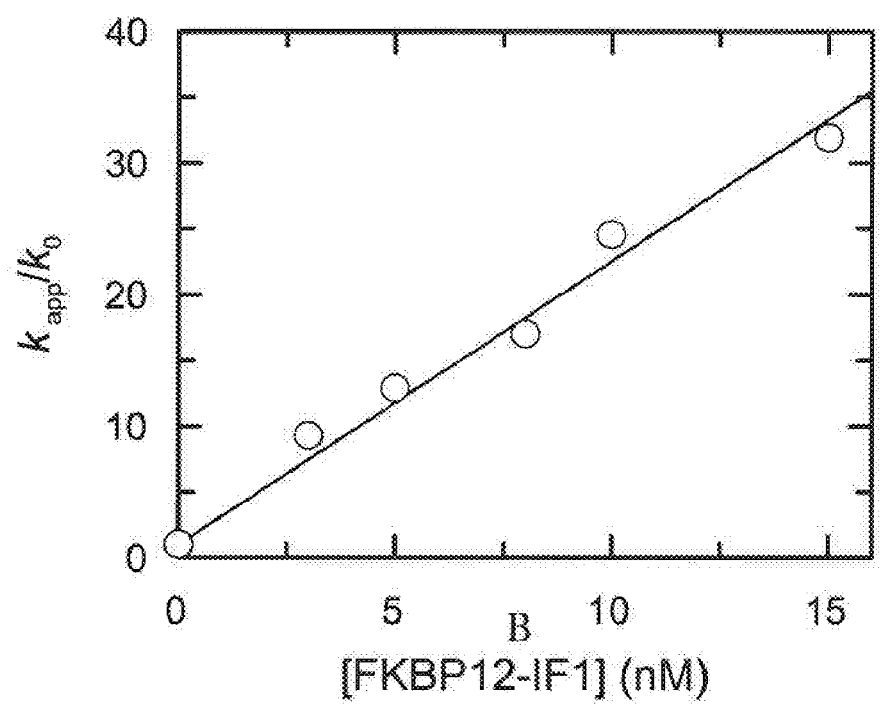

Deletion of the putative IF domain virtually abolishes the folding activity of SlyD*. The SlyD mutant lacking the IF domain represents the FKBP or FKBP-like domain of SlyD. How is, in contrast, the folding activity of hFKBP12 affected by insertion of this very IF element in the flap region? In agreement with published data (Scholz et al. (1997) *EMBO J.* 16, 54-58), catalysis of RCM-T1 refolding by hFKBP12 is rather modest (FIG. 6A). Analysis of the apparent first-order rate constants of refolding yields a specificity constant of $0.014 \times 10^6$ $M^{-1}s^{-1}$ (FIG. 6B). In contrast, the IF-loop insertion variant FKBP12-IF1 according to the invention catalyzes RCM-T1 refolding extremely well (FIG. 7A). Less than 1 nM FKBP12-IF1 are sufficient to double the folding rate of RCM-T1. The specificity constant is higher than $2.5 \times 10^6$ $M^{-1}s^{-1}$ (FIG. 7B and Table 1). This outstanding value even exceeds the catalytic efficiency of the trigger factor, which amounts to $1.2 \times 10^6$ $M^{-1}s^{-1}$ (Stoller et al. (1995) *EMBO J.* 14, 4939-4984; Zarnt et al. (1997) *J. Mol. Biol.* 271, 827-837; Scholz et al. (199.7) *EMBO J.* 16, 54-58). Thus, by constructing a chimeric fusion protein according to the invention, we converted a modest non-human prolyl isomerase and poor human chaperone into an outstanding folding helper with exceptionally good prolyl isomerase and chaperone properties.

According to the invention, the principle of combining a polypeptide binding domain of a non-human chaperone and a human PPIase domain can be extended to other examples. In analogy with the construction pattern of FKBP12-IF1 we grafted the putative IF loop domain of SlpA onto the folding scaffold of hFKBP12. SlpA (the acronym stands for SlyD-like protein A) is a close relative of SlyD. Information on SlpA is scarce, but owing to its homology with SlyD it is supposed to serve a role as a PPIase chaperone in the *E. coli* cytosol. We purified and characterized a hexa-histidine tagged (SEQ ID NO: 24) SlpA variant from *E. coli*. However, this putative PPIase exhibited a very poor activity in the RCM-T1 refolding assay (Table 1). The chimera encompassing elements from hFKBP12 and SlpA was termed hFKBP12-IF4. It comprises the modules G1-G83 from hFKBP12, V72-T132 from SlpA, and L97-E107 from hFKBP12 (for sequence information, see SEQ ID NO: 13). Expression, purification to homogeneity and refolding of the hexa-histidine-tagged (SEQ ID NO: 24) protein were essentially carried out as described for FKBP12-IF1. Assessment by near-UV CD yielded a spectrum which unambiguously points to a compact fold of the designed protein (spectrum not shown).

Figure 10:
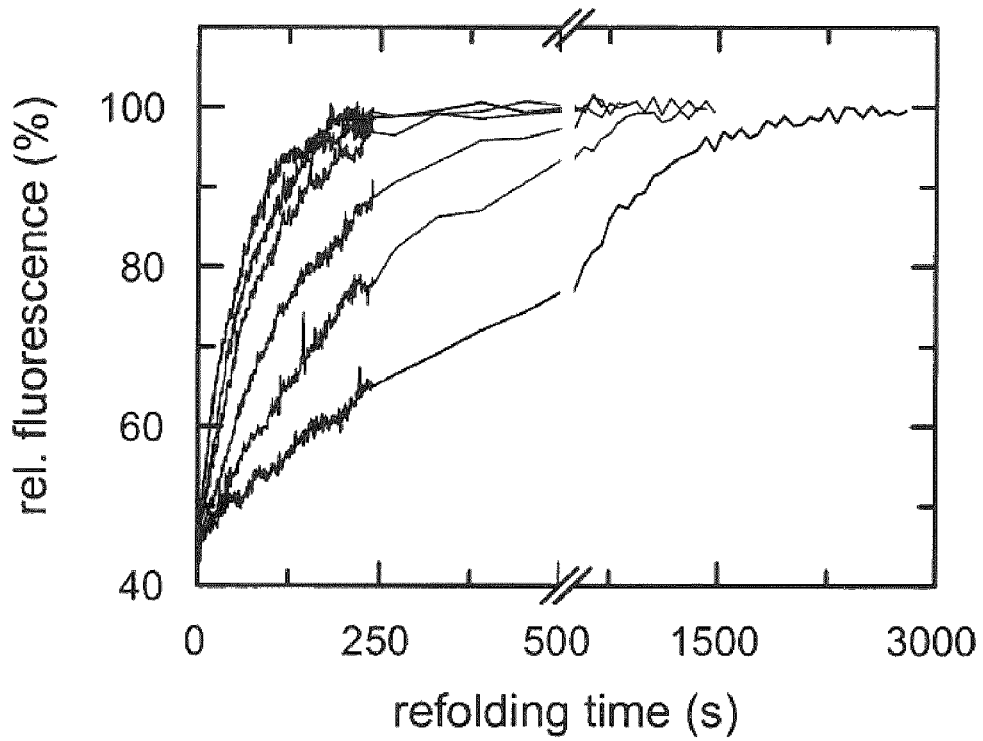
FIG. 10: Refolding kinetics of RCM-T1 in the presence of increasing concentrations of the chimeric protein hFKBP12-IF4 (with SlpA insert) according to the invention at 15° C. (A) The kinetics of refolding of 100 nM RCM-T1, as followed by the change in fluorescence at 320 nm, are shown in the presence of 0, 3, 6, 10, 15 and 20 nM hFKBP12-IF4. (B) Dependence on hFKBP12-IF4 concentration of the rate of slow folding. The ratio of the observed rate constants in the presence, $k_{app}$, and in the absence, $k_0$, of hFKBP12-IF4 is shown as a function of the hFKBP12-IF4 concentration. A value of 850000 M$^{-1}$s$^{-1}$ is obtained for $k_{cat}/K_M$ from the slope of the line in (B). Refolding of RCM-T1 in 0.1 M Tris-HCl, pH 8.0 was initiated by dilution to 2.0 M NaCl in the same buffer.
Figure 10:
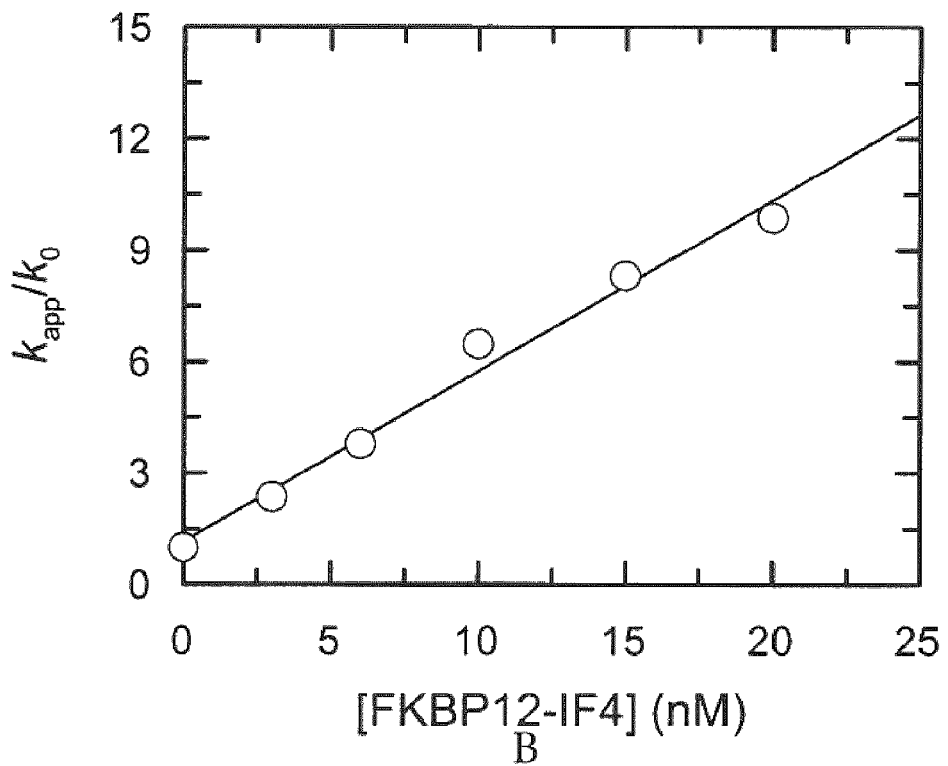

When assessed in the RCM-T1 refolding assay, hFKBP12-IF4 exhibited a surprisingly high folding activity (FIG. 10 A). Its specificity constant ($k_{cat}/K_M$) was 800.000 $M^{-1}s^{-1}$ (see table 1) and virtually equals the catalytic efficiency of SlyD, which is a very potent folding helper (Scholz et al., Biochemistry 2006, 45, 20-33). Again, combination of a putative polypeptide binding domain (from SlpA) with a sluggish prolyl isomerase (hFKBP12) yields an outstanding folding helper with both high enzyme and chaperone activity. We conclude that by combination of hFKBP12 with IF loop domains from diverse SlyD homologues humanized folding helpers with exceptional folding activities can be obtained.

A further example of the principle of combining a polypeptide binding domain of a non-human chaperone and a human PPIase domain is a chimeric fusion protein called hFKBP12-IF5. According to the construction pattern of FKBP12-IF1 and FKBP12-IF4 we grafted the putative IF loop domain of *Thermococcus* FKBP18 onto the folding scaffold of hFKBP12. *Thermococcus* FKBP18 is a thermostable homologue of SlyD bearing a putative IF domain in the flap region near the prolyl isomerase active site.

The resulting chimera was termed hFKBP12-IF5. It comprises the modules G1-G83 from hFKBP12, M84-T140 from *Thermococcus* FKBP18, and L97-E107 from hFKBP12 (for sequence information, see SEQ ID NO: 14 for *Thermococcus* FKBP18 and SEQ ID NO: 15 for hFKBP12-IF5). Expression, purification to homogeneity and refolding of the hexa-histidine-tagged (SEQ ID NO: 24) protein were essentially carried out as described for FKBP12-IF1.

Figure 11:
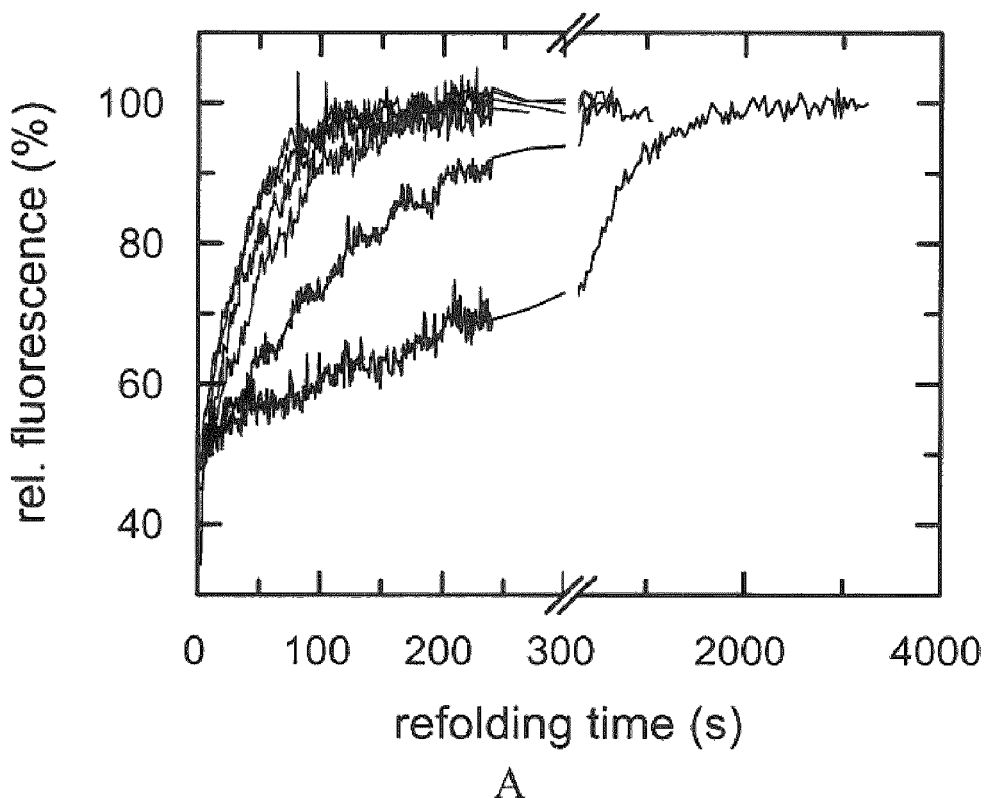
FIG. 11: Refolding kinetics of RCM-T1 in the presence of increasing concentrations of the chimeric protein hFKBP12-IF5 (with *Thermococcus* FKBP18 insert) according to the invention at 15° C. (A) The kinetics of refolding of 100 nM RCM-T1, as followed by the change in fluorescence at 320 nm, are shown in the presence of 0, 10, 25, 30, 35 and 40 nM hFKBP12-IF5. (B) Dependence on hFKBP12-IF5 concentration of the rate of slow folding. The ratio of the observed rate constants in the presence, $k_{app}$, and in the absence, $k_0$, of hFKBP12-IF5 is shown as a function of the hFKBP12-IF5 concentration. A value of 660000 $M^{-1}s^{-1}$ is obtained for $k_{cat}/K_M$ from the slope of the line in (B). Refolding of RCM-T1 in 0.1 M Tris-HCl, pH 8.0 was initiated by dilution to 2.0 M NaCl in the same buffer.
Figure 11:
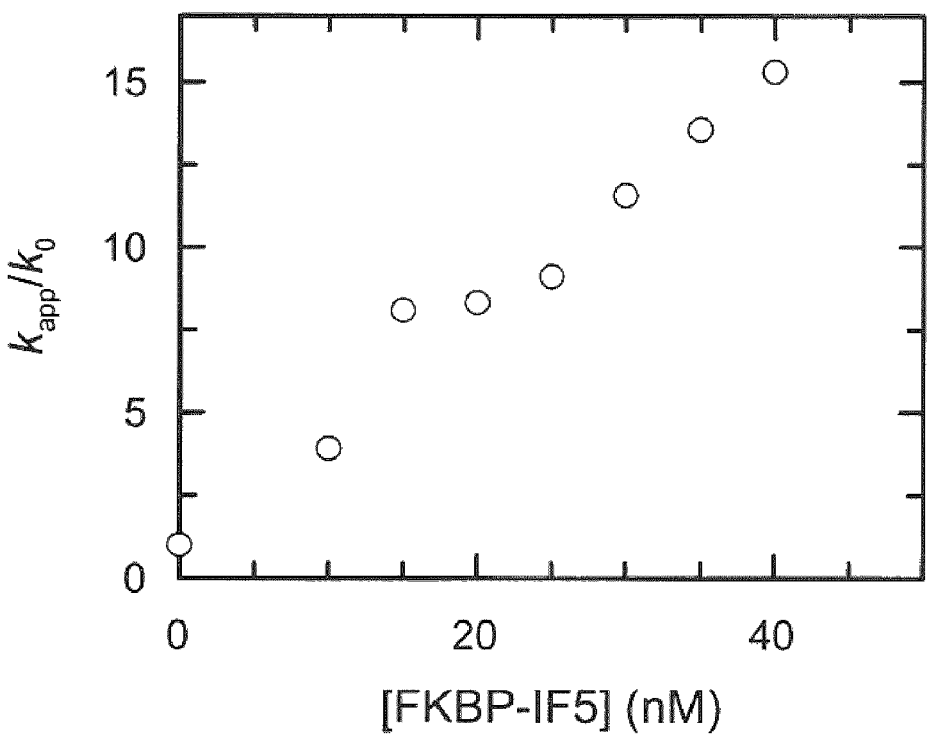

When assessed in the RCM-T1 refolding assay, hFKBP12-IF5 exhibited a surprisingly high folding activity (FIG. 11). Its specificity constant ($k_{cat}/K_M$) was 660,000 $M^{-1}s^{-1}$ and virtually equals the catalytic efficiency of SlyD, which is a very potent folding helper according to recent literature data (Scholz et al., Biochemistry 2006, 45, 20-33). Again, combination of a putative polypeptide binding domain (from the thermostable TcFKBP18) with a sluggish prolyl isomerase (hFKBP12) yields an outstanding folding helper with both high enzyme and chaperone activity. Our studies unambiguously show that the combination of hFKBP12 with IF loop domains from diverse SlyD homologues yield humanized folding helpers with exceptional folding activities.

The very same principle also holds with FKBP-like domains, which occur in many prokaryotic and eukaryotic prolyl isomerases. For instance, FkpA and trigger factor are two *E. coli* proteins comprising FKBP-like domains. It has been shown before, that these FKBP-like domains, when separated from the rest of the molecule, exhibit a very modest folding activity (Scholz et al., EMBO J. (1997) 16 (I) 54-58; Saul et al., J. Mol. Biol (2004) 335, 595-608). This is in perfect agreement with human FKBP12, which is a modest prolyl isomerase lacking any chaperone activity. By grafting of any SlyD IF domain (also termed polypeptide binding segment) onto a FKBP-like domain as a folding scaffold excellent folding helpers may be obtained. These chimeras may be also used as folding helpers in recombinant protein biotechnology, e.g., as fusion proteins, additives in refolding buffers and the like.

The principle of domain grafting also holds for SlyD itself. The SlyD deletion variant lacking the IF domain (SlyD ΔIF) represents the genuine FKBP domain, which can be combined with IF domains from other FKBP chaperones to yield a folding helper with outstanding catalytic efficiency. The current invention therefore also encompasses the use of SlyD, in particular the SlyD variant lacking the IF domain for producing folding helper with a catalytic efficiency that exceeds the catalytic efficiency of the naturally occurring wild type molecules the resulting chimeric folding helper is made of.

Table 1 summarizes the results obtained for all proteins measured in the RCM-T1 assay.

TABLE 1

| PPIase variant | Specificity constant $k_{cat}/K_M (M^{-1}s^{-1})$ |
|---|---|
| hFKBP12 | 14,000 |
| hFKBP12 (C22A) | 14,000 |
| SlyD* (SlyD 1-165) | 680,000 |
| SlyD* ΔIF loop | 500 |
| hFKBP12-IF1 (C22A)/invention | 2,500,000 |
| SlpA | <1000 |
| hFKBP12-IF4/invention | 850,000 |
| TcFKBP18 | 600,000 |
| hFKBP12-IF5/invention | 660,000 |

Example 4

Immune-Logical Reactivity of FKBP12-IF1/HIVgp41 Fusion Proteins

This example shows the addition of an HIV protein, i.e., the envelope protein gp41 as a target protein to the chimeric fusion protein FKBP12-IF1 according to the invention. The tandem FKBP12-IF1-gp41 fusion module was purified and refolded as described for the SlyD and hFKBP12 protein variants. It was used to detect anti-gp41 antibodies, which abundantly occur in HIV-1 positive sera. The immunological reactivity was challenged in an automated ELECSYS 2010 analyzer (Roche Diagnostics GmbH, Germany) using the double-antigen sandwich format.

Signal detection in the ELECSYS immunoassay is based on electrochemiluminescence. The biotin conjugate (i.e., the capture antigen) is immobilized on the surface of a streptavidin-coated magnetic bead, whereas the signaling antigen bears a complexed ruthenium cation as the luminescent moiety. In the presence of anti-gp41 antibodies, the chromogenic ruthenium complex is bridged to the solid phase and emits light at 620 nm after excitation at a platinum electrode. The signal output is in arbitrary light units.

For their use as ELECSYS antigens, the soluble gp41 fusion proteins under study were concentrated and modified with N-hydroxysuccinimide-activated biotin and ruthenium moieties as described by Scholz et al. (2005), *J. Mol. Biol.* 345, 1229-1241. The concentration of the gp41 variants in the immunoassay measurements was about 500 ng/ml. At least five negative sera were used as controls. In order to further minimize false positive results, polymerized unlabeled *E. coli* SlyD* was added to the samples as an anti-interference substance.

Figure 9:
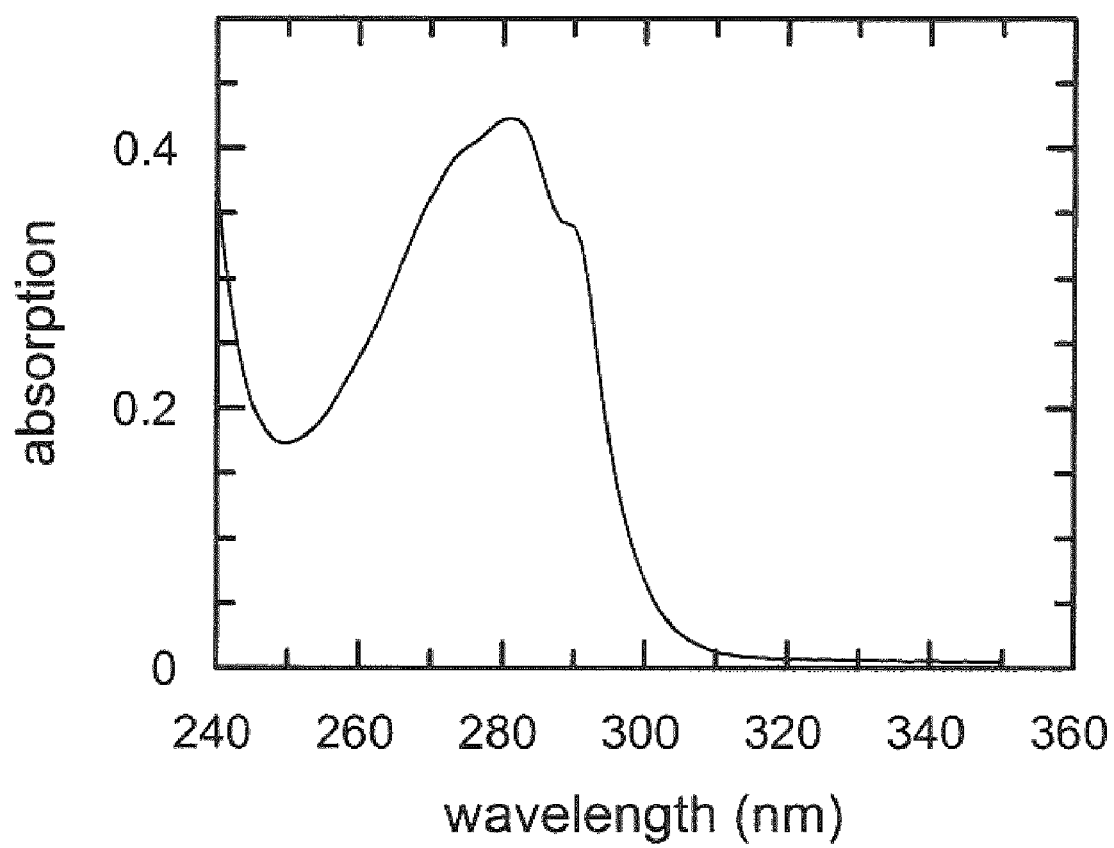
FIG. 9: UV spectrum of the chimeric fusion protein hFKBP12-IF1-gp41 according to the invention. After matrix-coupled refolding and imidazole elution, the protein is soluble in aqueous buffer. In order to keep the absorption within the Lambert-Beer range of linearity, the protein stock solution was diluted 20-fold to 5 µM in 50 mM sodium phosphate pH 7.5, 100 mM NaCl, 1.5 mM EDTA at room temperature. Protein aggregates or high-molecular associates are light straying particles, which would lead to a sloping baseline in the wavelength region between 310 and 350 nm. The shape of the spectrum proves the absence of any aggregates and highlights the solubility of hFKBP12-IF1-gp41.

It turned out that the chimeric fusion FKBP12-IF1 according to the invention is well suited as a fusion partner for aggregation-prone proteins. When wild type-hFKBP12 was fused to the gp41 ectodomain fragment, the resulting fusion proteins aggregated quantitatively after matrix-coupled refolding and imidazole elution. Obviously, hFKBP12 is not able to confer solubility on an extremely hydrophobic target such as the gp41 ectodomain fragment. In contrast, we find that chimeric fusion proteins according to the invention comprising FKBP12-IF1 and the HIV-1 gp41 ectodomain fragment 536-681 (schematic FIG. 8) are perfectly soluble and do not tend to aggregate as judged by UV spectroscopy (FIG. 9). When assessed in an automated ELECSYS analyzer, they turn out to be well suited for diagnostic applications in HIV-1 serology (data not shown). This further highlights the outstanding properties of the chimeric fusion proteins according to the invention.

What is claimed is:

1. A recombinant DNA molecule encoding the polypeptide as set forth in SEQ ID NO: 5.

\* \* \* \* \*